United States Patent
Lynch et al.

(10) Patent No.: US 6,773,627 B2
(45) Date of Patent: Aug. 10, 2004

(54) CUBIC LIQUID CRYSTALLINE COMPOSITIONS AND METHODS FOR THEIR PREPARATION

(75) Inventors: Matthew Lawrence Lynch, Cincinnati, OH (US); Patrick Thomas Spicer, Cincinnati, OH (US)

(73) Assignee: Children's Hospital Research Foundation, Cincinnati, OH (US)

( * ) Notice: Subject to any disclaimer, the term of this patent is extended or adjusted under 35 U.S.C. 154(b) by 0 days.

(21) Appl. No.: 10/728,155

(22) Filed: Dec. 4, 2003

(65) Prior Publication Data

US 2004/0079921 A1 Apr. 29, 2004

Related U.S. Application Data

(63) Continuation of application No. 09/789,883, filed on Feb. 21, 2001, now abandoned.
(60) Provisional application No. 60/215,113, filed on Jun. 29, 2000.

(51) Int. Cl.$^7$ ................................................ C09K 19/52
(52) U.S. Cl. ................... 252/299.01; 514/937; 514/964
(58) Field of Search ................. 424/422, 423, 424/450, 455; 252/299.01; 428/1; 514/937, 964

(56) References Cited

U.S. PATENT DOCUMENTS

| 4,296,095 A | 10/1981 | Hoppe et al. |
| 4,557,935 A | 12/1985 | af Ekenstam et al. |
| 4,608,211 A | 8/1986 | Handjani et al. |

(List continued on next page.)

FOREIGN PATENT DOCUMENTS

| AU | 718444 | 10/1996 | | |
| EP | 0 103 910 | * | 6/1983 | ............ A61K/7/48 |
| EP | 0 103 910 A1 | | 3/1984 | |

(List continued on next page.)

OTHER PUBLICATIONS

Alfons and Engstrom, "Drug Compatibility with the Sponge Phases Formed in Monolein, Water, and Propylene Glycol or Poly(ethylene glycol)," J. Pharm. Sci. vol. 87, No. 12, 1527–1530 (Dec. 1998).

Fontell, "Cubic phases in surfactant and surfactant–like lipid systems," Colloid. Polym. Sci. 268:264–285 (1990).

Tabony, "Formation of cubic structures in microemulsions containing equal volumes of oil and water," Nature, vol. 319, 400 (Jan. 30, 1986).

Brown, ed., *Advances in Liquid Crystals*, vol. 1, Ekwall, "Composition, Properties and Structures of Liquid Crystalline Phases in systems of Amphiphilic Compounds," pp 1–139, Academic Press (1975).

Lindblom et al., "Phase Equilibria of Membrane Lipids from *Acholeplasma laidlawii*: Importance of a Single Lipid Forming Nonlamellar Phases," Biochemistry 25, 7502–7510 (1986).

Engström et al., "A study of polar lipid drug carrier systems undergoing a thermoreversible lamellar–to–cubic phase transition," Int. J. Pharmaceutics, 86 137–145 (1992).

(List continued on next page.)

*Primary Examiner*—Mark F. Huff
*Assistant Examiner*—Jennifer R. Sadula
(74) *Attorney, Agent, or Firm*—Frost Brown Todd LLC

(57) ABSTRACT

Cubic liquid crystalline gel precursors, bulk cubic liquid crystalline gels, and dispersions of cubic liquid crystalline gel particles, and methods for their preparation, are disclosed. The precursors, gels, and dispersions can be used as skin penetration enhancers. The precursors, gels, and dispersions are prepared by methods employing hydrotropes that do not detrimentally affect the cubic liquid crystalline structure of the gels and particles.

49 Claims, 12 Drawing Sheets

U.S. PATENT DOCUMENTS

| | | | |
|---|---|---|---|
| 4,830,857 A | 5/1989 | Handjani et al. | |
| 4,931,282 A | 6/1990 | Asmus et al. | |
| 4,931,284 A | 6/1990 | Ekman et al. | |
| 5,001,062 A | 3/1991 | Larsson et al. | |
| 5,032,115 A | 7/1991 | Hakansson et al. | |
| 5,055,228 A | 10/1991 | Zabotto et al. | |
| 5,079,227 A | 1/1992 | Handjani et al. | |
| 5,137,725 A | 8/1992 | Handjani et al. | |
| 5,151,272 A | 9/1992 | Engstrom et al. | |
| 5,190,755 A | 3/1993 | Molin et al. | |
| 5,196,201 A | * 3/1993 | Larsson et al. | 424/422 |
| 5,230,895 A | 7/1993 | Czarnecki et al. | |
| 5,260,282 A | 11/1993 | Attstrom et al. | |
| 5,290,565 A | 3/1994 | Zysman et al. | |
| 5,362,494 A | 11/1994 | Zysman et al. | |
| 5,371,109 A | * 12/1994 | Engstrom et al. | 514/786 |
| 5,411,742 A | 5/1995 | Sebag et al. | |
| 5,439,672 A | 8/1995 | Zabotto et al. | |
| 5,531,925 A | * 7/1996 | Landh et al. | 252/299.01 |
| 5,539,129 A | 7/1996 | Zysman et al. | |
| 5,593,663 A | * 1/1997 | Leng et al. | 424/65 |
| 5,601,833 A | 2/1997 | Ribier et al. | |
| 5,614,215 A | 3/1997 | Ribier et al. | |
| 5,629,015 A | 5/1997 | Ribier et al. | |
| 5,637,316 A | 6/1997 | Ribier et al. | |
| 5,650,166 A | 7/1997 | Ribier et al. | |
| 5,658,575 A | 8/1997 | Ribier et al. | |
| 5,665,699 A | 9/1997 | Philippe et al. | |
| 5,679,374 A | 10/1997 | Fanchon et al. | |
| 5,679,691 A | 10/1997 | Ribier et al. | |
| 5,753,241 A | 5/1998 | Ribier et al. | |
| 5,753,259 A | * 5/1998 | Engstrom et al. | 424/500 |
| 5,756,108 A | 5/1998 | Ribier et al. | |
| 5,759,526 A | 6/1998 | Simonnet et al. | |
| 5,807,573 A | * 9/1998 | Ljusberg-Wahren et al. | 424/450 |
| 5,834,013 A | 11/1998 | Ribier et al. | |
| 5,866,158 A | * 2/1999 | Ribier et al. | 424/450 |
| 5,871,760 A | 2/1999 | Doughty et al. | |
| 5,906,831 A | * 5/1999 | Larsson et al. | 424/450 |
| 5,919,434 A | * 7/1999 | Dugstad et al. | 424/9.52 |
| 5,925,364 A | 7/1999 | Ribier et al. | |
| 5,948,416 A | 9/1999 | Wagner et al. | |
| 5,993,831 A | 11/1999 | Ribier et al. | |
| 6,051,250 A | 4/2000 | Ribier et al. | |
| 6,482,517 B1 | 11/2002 | Anderson | |

FOREIGN PATENT DOCUMENTS

| | | |
|---|---|---|
| EP | 0 534 823 B1 | 3/1993 |
| EP | 0 729 747 A1 | 9/1996 |
| EP | 0 867 168 A2 | 3/1998 |
| GB | 2 189 457 A | 4/1987 |
| WO | WO 9218103 A1 | 10/1992 |
| WO | WO 9220319 A1 | 11/1992 |
| WO | WO 9715386 A1 | 5/1997 |
| WO | WO 9810281 A1 | 3/1998 |
| WO | WO 9830206 A1 | 7/1998 |
| WO | WO 9847487 A1 | 10/1998 |
| WO | WO 9912640 A1 | 3/1999 |
| WO | WO 9947004 A1 | 9/1999 |
| WO | WO 98SE1632 | 2/2000 |
| WO | WO 0012536 A2 | 3/2000 |
| WO | WO 01/68139 A1 | 9/2001 |

OTHER PUBLICATIONS

Engström et al., "Phase behavior of the lidocaine–monoolein–water system," Int. J. Pharmaceutics, 79 113–122 (1992).

Angelov, et al., "X–ray Diffraction Study of the Effect of the Detergent Octyl Glucoside on the Structure of Lamellar and Nonlamellar Lipid/Water Phases of Use for Membrane Protein Reconstitution," Langmuir, 15, 8225–8234, 1999.

Aota–Nakano, et al., "Effects of electrostatic interaction on the phase stability and structures of cubic phases of monoolein/oleic acid mixture membranes," Biochimica et Biophysica Acta, 1461, 96–102, 1999.

Bellare, J.R.; Davis, H.T.; Scriven, L. E.; Talmon, Y., "Controlled environment vitrification technique," J. Electron Microsc. Tech., 10, 87–111, 1988.

Briggs, et al., "The Temperature–Composition Phase Diagram and Mesophase Structure Characterization of the Monoolein/Water System," J. Phys. II France, 6, 723–751, 1996.

Chang, et al., "Binding of drugs to monoglyceride based drug delivery systems," International Journal of Pharmaceutics, 147, 135–142, 1997.

Drummond, et al., "Surfactant Self–Assembly Objects as Novel Drug Delivery Vehicles," Current Opinion in Colloid and Interfacial Science, 4, 449–456, 2000.

Evans, The Colloidal Domain. $2^{nd}$ ed., Wiley, NY, pp. 575–588, 1999.

Funari,S. S. and Gert, R., "X–ray Studies on the C12EO2/Water System", J. Phys. Chem. B, 101, 732, 1997.

Gustafsson, et al, "Submicron Particles of Reversed Lipid Phases in Water Stabilized by a Nonionic Amphiphilic Polymer," Langmuir, 13, 6964–6971, 1997.

Gustafsson, et al. "Phase Behavior and Aggregate Structure in Aqueous Mixtures of Sodium Cholate and Glycerol Monooleate," Journal of Colloid and Interface Science, 211, 326–335, 1999.

Gustafsson, et al. "Defective Lamellar Phases and Micellar Polymorphism in Mixtures of Glycerol Monooleate and Cetyltrimethylammonium Bromide in Aqueous Solution," Langmuir, 14. 4987–1996, 1998.

Hecht, E., Optics, $2^{nd}$ ed., Addison–Wesley Publishing Co., Reading, Massachusetts, pp. 282–289, 1984.

Hyde et al., The Language of Shape, Elsevier Amsterdam, chapters 1 and 4, 1997.

Landh, "Phase Behavior in the System Pine Oil Monoglycerides–Poloxamer 407–Water at 20 C" J. Phys. Chem., 98 8453–8467, 1994.

Landau, et al., "Lipidic cubic phases: A novel concept for the crystallization of membrane proteins," Proc. Natl. Acad. Sci. USA, 93, 14532–14535, 1996.

Laughlin, R.G., J. Colloid Interface Sci., 55 239–242, 1976.

Laughlin, R.G., The Aqueous Phase Behavior of Surfactants, Academic Press, New York, pp. 255 and 521–546, 1994.

Lee, et al., "Combined effect of oleic acid and polyethylene glycol 200 on buccal permeation of [D–Ala2, D–Leu5] enkephalin from a cubic phase of glyceryl monooleate," International Journal of Pharmaceutics, 204, 137–144, 2000.

Lndell, et al., "Influence of a charged phospholipid on the release pattern of timolo maleate from cubic liquid crystalline phases." S. Prog. Colloid Polym. Sci., 108, 111–118, 1998.

Lipowsky, et al., eds., "The Structure and Conformation of Amphiphilic Membranes," Proceedings of the International Workshop on Amphiphilic Membranes, Julich, Germany, Sep. 16–18, 1991. Templer, et al. "Swollen Lyotropic Cubic Phases in Fully Hydrated Mixtures of Monoolein. Dioleoylphosphatidylcholine, and Dioleoylphosphatidylethanolamine." 262–265.

Luzzati et al., *J. Mol. Biol.*, 229, 540–551, 1993.

Lynch et al., "Aqueous Phase Behavior and Cubic PhaseContaining Emulsions in the C12E2–Water System," *Langmuir*, vol. 16, No. 7, pp. 3537–3542, 2000.

Pearson, J. T., Smith, J. M., "The Effect of Hycrotropic Salts on the Stability of Liquid Crystalline Systems," *J. Pharm. Pharmac.*, 26, 123–124, 1974.

Pitzalis, et al., "Characterization of the Liquid–Crystalline Phases in the Glycerol Monooleate/Diglycerol Monooleate/Water System," *Langmuir* 16, 6358–6365, 2000.

Puvvada, et al., "Ionotropic Gelation in a Bioowtinuous Cubic Phase," *J. Phys. Chem.*, 97, 11103–11107, 1993.

Razumas, et al., "A Cubic Monoolein–Cylochrome c–Water Phase: X–ray diffraction, FT–IR Differential Scanning Calorimetricm, and Electrochemical Studies," *J. Phys. Chem.*, 100, 11766–11774, 1996.

Razumas et al., "Effects of distearoylphosphosphatixtylglycerol and lysozyme on the structure of the monoolein–water cubic phase: X–ray diffraction and Raman scattering studies," *Chemistry and Physics of Lipids*, 84, 123–138, 1996.

Razumas, et al., "Structural characteristics and redox activity of the cubic monoolein/ubiquinone–10/water phase," *Progr. Colloid Polym. Sci.*, 108, 75–82, 1998.

Rummel, et al., "Lipid Cubic Phases: New Matrices for the Three–Dimensional Crystallization of Membrane Proteins," *Journal of Structural Biology* . 121, 82–91, 1998.

Rosevear, F.B., *J. Am. Oil Chemists Soc.*, 31, 628–638, 1954.

Soderberg, et al., "Phase properties and structure of a monoglyceride/sucroses/water system," *Chemistry and Physics of Lipids*, 55, 97–101, 1990.

Winey, Thomas and Fetters, "Morphologies in Binary Blends", *J. Chem. Phys.*, vol. 95, No. 12, Pg. 9368, 1991.

J.S. Kim, et al., *Drug Formulations that Form a Dispersed Cubic Phase when Mixed with Water*, Proceed. Int'l. Symp. Control. Rel. Bioact. Mater., 27 (2000) Controlled Release Society, Inc., pp. 1118 & 1119.

* cited by examiner

CUBIC LIQUID CRYSTALLINE COMPOSITIONS AND METHODS FOR THEIR PREPARATION

CROSS REFERENCE TO RELATED APPLICATION

This application is a continuation of U.S. patent application Ser. No. 09/789,883, filed Feb. 21, 2001, now abandoned. This application also claims the benefit of provisional 60/215,113 filed on Jun. 29, 2000.

FIELD OF THE INVENTION

This invention relates to cubic liquid crystalline compositions, precursors thereof, and methods for their preparation. More particularly, this invention relates to improved methods for preparing dispersions of cubic liquid crystalline gel particles.

BACKGROUND OF THE INVENTION

"Amphiphilic substance" means a molecule with both hydrophilic and hydrophobic (lipophilic) groups. Amphiphilic substances spontaneously self-associate in aqueous systems forming various types of aggregates. Examples of these aggregates include lamellar phases, hexagonal phases, and cubic phases. These phases are thermodynamically stable. The long-range order in these phases, in combination with liquid-like properties in the short-range order, gave rise to the notation "liquid crystalline phases".

Cubic Gel Precursors

Liquid crystalline phases (i.e., bulk cubic liquid crystalline gels and dispersions of cubic liquid crystalline gel particles) can be formed from precursors including an amphiphilic molecule such as a lipid and a polar liquid. The cubic liquid crystalline gel phase structures can form in response to some event, such as a temperature change or dilution of the precursor. In some applications, a cubic gel precursor forms a bulk cubic liquid crystalline gel only when needed for the specific application. For example, precursors have been used in antiperspirants, in which a water-insoluble liquid crystalline phase forms when the precursor contacts sweat (salt water). The resulting bulk liquid crystalline gel has a cubic or hexagonal liquid crystal structure that blocks pores.

Precursors have also been used to deliver a therapeutic agent to treat periodontal disease, for example, by putting the precursor comprising a monoglyceride and an active ingredient into a reservoir such as a periodontal pocket. The precursor forms bulk cubic liquid crystalline gel on contact with saliva and then provides controlled release of the therapeutic agent.

However, in these applications, some uncontrolled stimulus (such as sweating or salivating) is always required for the precursor to form bulk cubic liquid crystalline gel. No control can be exercised over the properties of the bulk cubic liquid crystalline gel formed. Furthermore, particulate cubic liquid crystalline gel cannot be formed directly from the precursor. Therefore, it is an object of this invention to provide precursors that can directly form either bulk or particulate cubic liquid crystalline gels. It is a further object of this invention to provide a method for using the precursor to prepare bulk and particulate cubic liquid crystalline gels with controlled properties.

Bulk Cubic Liquid Crystalline Gel

The liquid crystalline phases have distinct hydrophilic and hydrophobic domains, which give them the ability to dissolve (solubilize) or disperse water-soluble, oil-soluble, and amphiphilic compounds. Liquid crystalline phases are highly ordered structures that restrict the diffusion of added ingredients, thereby making them useful for controlled-release purposes. Cubic liquid crystalline phases can be prepared as pastes and thus are particularly useful as delivery vehicles due to their rheological properties. Cubic liquid crystalline phases are also advantageous in that they are mechanically robust and resistant to physical degradation.

Bulk cubic liquid crystalline gels prepared in advance (i.e., before administration rather than in situ, as in the treatment of periodontal disease described above) can also be used as controlled release reservoirs of pharmaceutical materials. However, bulk cubic liquid crystalline gels are typically difficult to prepare due to the properties of the raw materials and rheological properties of the gels themselves. Lipids that yield cubic liquid crystalline phases, such as monoglycerides, are typically waxy solids at room temperature. Therefore, the bulk cubic liquid crystalline gel is prepared by equilibrating at high temperature or over many hours, or both, because transport of water is slow through solid lipids. Processes that require long hold times at high temperatures to manufacture bulk cubic liquid crystalline gels are not economically practical, particularly on a commercial scale. Therefore, it is a further object of this invention to provide a method for forming a bulk cubic liquid crystalline gel at relatively low temperature (e.g., room temperature) and in a relatively short amount of time (e.g., within minutes). It is a further object of this invention to provide an economical and practical method for preparing commercial scale quantities of bulk cubic liquid crystalline gels.

Bulk cubic liquid crystalline phases are high-viscosity solid-like gels, which makes large-scale processing to form dispersed particles of cubic liquid crystalline phase difficult. Large scale processing of bulk solid and solid-like materials is difficult because of problems associated with adequate mixing and homogenizing. High energy input is required, and this energy can degrade liquid crystalline structures. For example, high energy input processes, such as those employing high shear can physically degrade crystalline structures. High energy input processes, such as those employing high temperatures can chemically degrade the compounds making up the liquid crystalline structures. Furthermore, high energy input processes are costly and require more precise control and maintenance. Therefore, it is an object of this invention to provide methods for preparing cubic liquid crystalline phase materials that are less costly and more efficient than the methods involving bulk solid processing.

Dispersed Cubic Liquid Crystalline Gel Particles

Lamellar phases have a bilayer sheet structure. When a lamellar phase is dispersed in excess water, the lamellar phase forms vesicles and liposomes. "Vesicle" means an enclosed shell comprised of one bilayer of amphiphilic molecules. "Liposome" means an enclosed shell comprised of more than one bilayer of amphiphilic molecules. Vesicles and liposomes can be spheroidal, ellipsoidal, or irregularly shaped; however, spheroidal shells are the most stable.

Vesicles and liposomes suffer from the drawback that they are non-equilibrium states, which means that, inevitably, they will degrade. Furthermore, vesicles and liposomes are relatively expensive to manufacture. Therefore, it is an object of this invention to provide a stable, less expensive alternative to vesicles and liposomes.

Bulk cubic liquid crystalline gel can also be dispersed to form particles. Dispersed particles of cubic liquid crystalline phases are structurally distinct from vesicles and liposomes. Dispersed cubic gel particles have a cubic or spherical outer structure with a bicontinuous cubic internal structure. The bicontinuous cubic internal structure has distinct hydrophilic and lipophilic domains, and is described in S. Hyde et al., *The Language of Shape*, Elsevier, Amsterdam, 1997, chapters 1 and 4.

Typically, cubic liquid crystalline gel particles are formed via fragmentation and dispersion of homogeneous bulk cubic liquid crystalline gel. Fragmentation is carried out in combination with a fragmentation agent such as polysaccharides, proteins, amphiphilic macromolecules and lipids, amphiphilic polymers, and amphiphilic compounds. Fragmentation also requires the use of a high energy input process by, for example, high shear milling or sonication.

Fragmenting and dispersing solid and solid-like materials, such as bulk cubic liquid crystalline gel, are difficult and impractical above very small processing scales (e.g., on the order of several grams, or less) without significant energy input and hold time. This makes commercial scale production of dispersed cubic gels expensive and impractical. Furthermore, high energy input processes can create non-equilibrium structures, such as vesicles and liposomes. Therefore, it is an object of this invention to develop a means for producing dispersed cubic liquid crystalline gel particles that does not require a fragmentation step. It is a further object of this invention to provide a method for forming cubic gel particles instantaneously by homogeneous nucleation upon dilution. It is a further object of this invention to provide an economical and practical method for preparing commercial scale quantities of cubic liquid crystalline gel particle dispersions.

SUMMARY OF THE INVENTION

It has been surprisingly found that cubic liquid crystalline phase gels can be prepared in the presence of a hydrotrope. (Hydrotropes are perversely well-known for their efficiency at disrupting liquid crystalline materials, see Pearson, J. T., Smith, J. M., "The Effect of Hydrotropic Salts on the Stability of Liquid Crystalline Systems," *J. Pharm. Pharmac.*, 26, 123–124 (1974).) This invention relates to compositions that can be in the form of a cubic gel precursor, a bulk cubic liquid crystalline gel, or a dispersion of cubic liquid crystalline gel particles. The precursor comprises: (A) a hydrotrope and (B) an amphiphile that is capable of forming cubic liquid crystalline phase structures. The bulk cubic liquid crystalline gel comprises ingredients (A), (B) and (C) a solvent. The dispersed cubic liquid crystalline gel particles comprise ingredients (A), (B), (C), and preferably (D) a stabilizer. This invention further relates to methods for preparing the above compositions. The methods of this invention are commercially advantageous in that bulk solids handling of ingredient (B) can be eliminated when ingredient (B) is a solid at room temperature, and the fragmentation step required by methods for dispersing bulk liquid crystalline materials to form dispersions of particles having liquid crystalline structures can be eliminated by preparing dispersions of cubic gel particles directly from the cubic gel precursor.

DETAILED DESCRIPTION OF THE INVENTION

Figure 1:
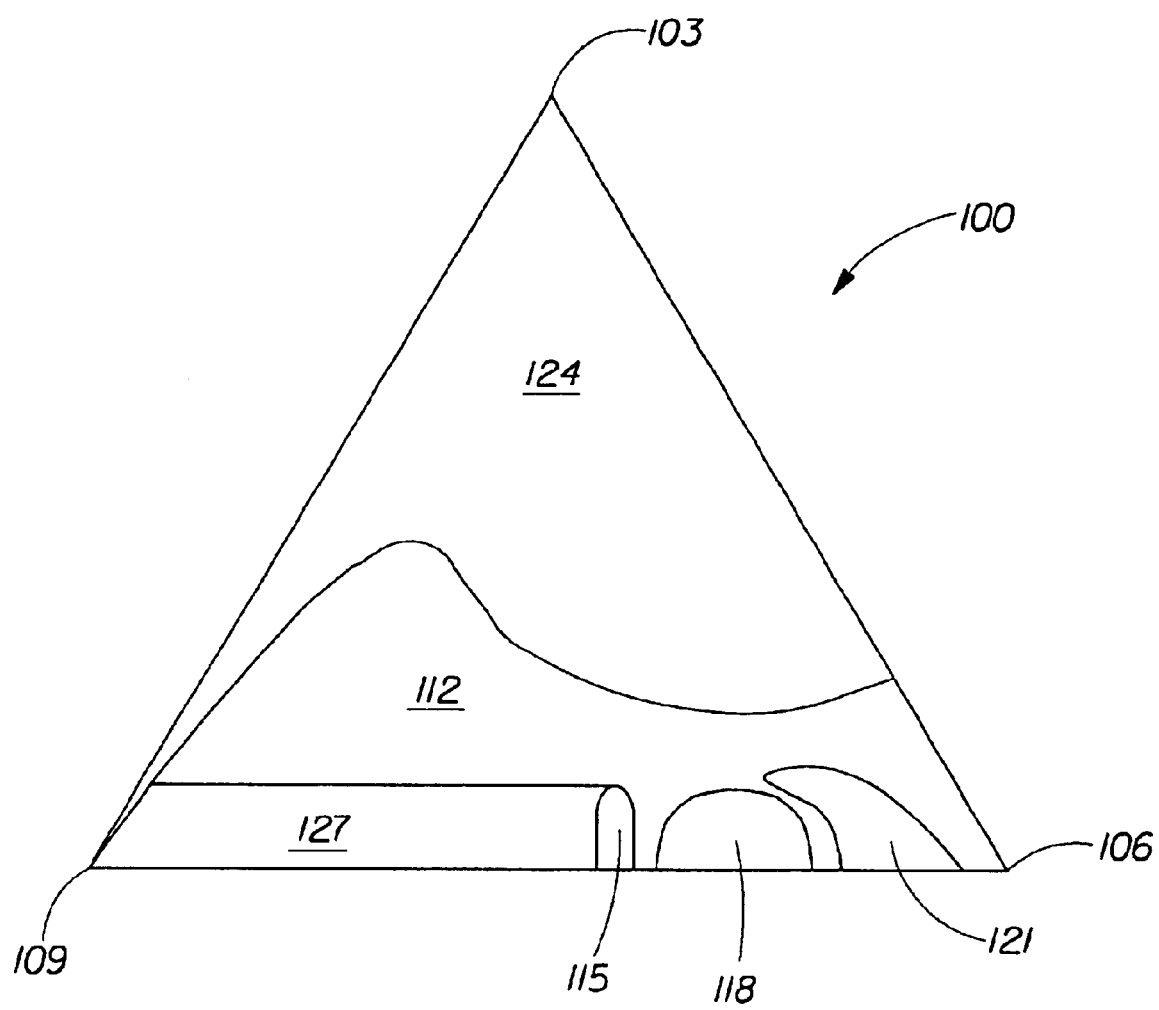
FIG. 1 is a ternary phase diagram showing the phase behavior of a system of monoolein, ethanol, and water.

Publications and patents are referred to throughout this disclosure. All U.S. Patents cited herein are hereby incorporated by reference.

All percentages, ratios, and proportions used herein are by weight unless otherwise specified. All measurements are made at 25° C., unless otherwise specified.

Definition and Usage of Terms

The following is a list of definitions for terms, as used herein:

"Amphiphile" means a molecule with both hydrophilic and hydrophobic (lipophilic) groups (e.g, surfactants, lipids, and polymers).

"Bulk cubic gel" means a viscous, structurally isotropic gel (clear, translucent, or opaque) having a normal or reversed cubic liquid crystalline structure, with a composition matching a cubic liquid crystalline region of a phase diagram representing the phase behavior of a hydrotrope, a surfactant, and a solvent. Bulk cubic gel may also be referred to herein as bulk cubic liquid crystalline gel.

"Colloidally stable" means that when cubic gel particles are dispersed in a solvent, the particles do not coalesce, flocculate, or agglomerate over time.

"Cubic gel precursor" means a formulation that will form a cubic liquid crystalline phase upon action by a stimulus. The stimulus can be the addition of some specified material such as additional hydrotrope, amphiphile, or solvent; the removal of some specified material such as a portion of the hydrotrope, amphiphile, or solvent; a temperature change; a pressure change; addition of salt; or a pH change in aqueous systems. Cubic gel precursor may also be referred to herein as cubic liquid crystalline gel precursor.

"Cubic gel particles" means the dispersed form of bulk cubic gel; technically they are cubic liquid crystalline gel in equilibrium with either the solvent, isotropic liquid phase, lamellar phase, or a combination of two of these.

"Gel" means a rheologically semisolid system. Gel includes cubic liquid crystalline materials such as bulk cubic gels and dispersions of cubic gel particles.

"Hydrotrope" means a surfactant-type molecule (comprising at least one hydrophilic group and at least one hydrophobic group), wherein the molecule has too short or too soluble a hydrophobic group or too insoluble or too large a hydrophilic group to display surfactant phase behavior. Hydrotropes are highly soluble in water and do not form aggregates in solution (e.g., micelles). Hydrotropes dissolve amphiphiles. Hydrotropes do not prevent formation of a cubic liquid crystalline phase upon dilution of a mixture of the hydrotrope and amphiphile with a solvent. The hydrotropes enhance the miscibility of weakly polar and otherwise water-insoluble molecules (such as monoolein) with aqueous solutions; this effect is commonly known as "salting-in". The hydrotrope is typically present in a substantial concentration (i.e., 1% or more) to display the hydrotropic properties described above.

"L1" means a dilute liquid phase.

"L2" means a concentrated liquid phase.

"Lipid" means any amphiphilic molecule of intermediate molecular weight that contains a substantial portion of aliphatic or aromatic hydrocarbon.

"Paste" means a liquid for topical application, preferably to the skin of an animal (preferably a human), whose viscosity is enhanced to the point that flow is largely inhibited by the presence of undissolved, as well as dissolved, solids.

"Stabilizer" means an agent that prevents aggregation, coalescence, and flocculation of dispersed phase particles. Stabilizers impart colloidal stability to dispersed cubic gel particles. Stabilizers include polymers, small particulates that absorb upon surfaces of the particles, ionic materials, and liquid crystalline phase adsorbed to the surfaces of the particles.

"Surfactant" means an amphiphile that exhibits the following properties in water (1) it reduces the interfacial tension, and (2) it self-assembles in solution at low concentrations.

"Thermodynamically stable" means that a system is at its lowest energy state.

Compositions

This invention relates to cubic gel precursors, bulk cubic gels, and cubic gel particles.

Cubic Gel Precursor

The cubic gel precursor comprises (A) a hydrotrope and (B) an amphiphile. The precursor may optionally further comprise (C) a solvent. The precursor must not form a cubic phase gel.

Hydrotrope

Ingredient (A) is a hydrotrope. The hydrotrope is capable of dissolving (B) the amphiphile. The hydrotrope must not prevent formation of a cubic liquid crystalline phase upon dilution of a mixture of the hydrotrope and amphiphile with the solvent. Preferred hydrotropes allow for formation of cubic gel particles dispersed in isotropic liquid phases.

Suitable hydrotropes include alcohols; polyols; alcohol ethoxylates; surfactants derived from mono- and polysaccharides; copolymers of ethylene oxide and propylene oxide; fatty acid ethoxylates; sorbitan derivatives; sodium butyrate; nicotinamide; procaine hydrogen chloride; and ethylene glycol, propylene glycol, glycerol, and polyglyceryl esters, and the ethoxylated derivatives thereof; combinations thereof; and others.

Examples of preferred hydrotropes include alcohols such as methanol and ethanol and polyols such as 1,4-butanediol and 1,2-hexanediol. Preferred alcohols include ethanol. Preferred polyols include 1,4-butanediol. Other preferred hydrotropes include sodium butyrate, nicotinamide, and procaine hydrogen chloride. Without wishing to be bound by theory, it is believed that the hydrotrope must have sufficient hydrophilic character for cubic liquid crystalline phase to form when the hydrotrope is present in amounts up to about 10%.

Whether a compound is suitable to use as ingredient (A) can be determined by one skilled in the art without undue experimentation. The determination can be made by preparing a composition comprising the compound to be tested for use as the hydrotrope, the selected amphiphile, and the selected solvent and allowing the composition to equilibrate, for example, by the method described below in Reference Example 1. If the composition forms a cubic phase or cubic phase in combination with another phase, then the hydrotrope is suitable to use in this invention. If the composition forms a cubic phase or cubic phase in combination with an isotropic liquid, then the hydrotrope is preferred.

Polarized light microscopy (PLM) can be used to determine whether the composition formed cubic phase. PLM can be carried out on a polarized light microscope or constructed light box, as described by Laughlin, R. G., J. Colloid Interface Sci., 55, 239–242 (1976). Polarized light microscope textures define the phase/colloidal state of sample. Lamellar and hexagonal phases give birefringence (see Hecht, E., Optics, $2^{nd}$ ed., Addison-Wesley Publishing Co., Reading, Mass., pp. 282–289 (1984)) and distinct textures such as Maltese Crosses (see Rosevear, F. B., J. Am. Oil Chemists Soc., 31, 628–638 (1954)). This is a consequence of the anisotropic phase structure of these particular phases, and their orientation relative to polarization of the light. However, L1, L2, L3, and cubic phases show no birefringence and appear dark in the microscope. Birefringence is a function of sample thickness, so sometimes it is difficult to see with a light microscope. Instead, the bulk sample can be placed in the aforementioned light box to secure a very thick sample.

Cubic phases are very viscous while the other phases are (i.e., L1, L2, and L3) are less viscous, like water. Therefore, lack of birefringence in combination with bulk solid-like rheological properties indicates the presence of cubic phase.

Amphiphile Capable of Forming Cubic Liquid Crystalline Phase

Ingredient (B) is an amphiphile that is capable of forming a cubic liquid crystalline phase. Ingredient (B) can be a single amphiphile or a combination (e.g., mixture) of two or more amphiphiles. Suitable amphiphiles are surfactants that must be capable of forming cubic liquid crystalline phases in the presence of ingredients (A) and (C) a solvent. Amphiphiles comprise a hydrophilic group and a lipophilic group. Suitable hydrophilic groups, and methods for the selection of suitable hydrophilic groups, are disclosed in Laughlin, R. G., The Aqueous Phase Behavior of Surfactants, Academic Press. New York, 1994, pp. 255; and in International Patent Publication No. WO 99/12640 at page 12.

TABLE 1

Anionic Hydrophilic Groups

| Functional Group | General Formula |
| --- | --- |
| Alkyl carboxylate salts | $RCO_2^-M^+$ |
| Alkanesulfonate salts | $RSO_3^+,M^+$ |
| Alkyl sulfate salts | $ROSO_3^-,M^+$ |
| N-Alkylsulfamate salts | $RNHSO_3^-,M^+$ |
| Akylsulfinate salts | $RSO_2^-,M^+$ |
| S-Alkylthiosulfate salts | $RSSO_3^-,M^+$ |
| Phosphonate salts | $RPO_3^-,M^+$ |
| Phosphate monoester salts | $ROPO_4^=,2M^+$ |
| Phosphinate salts | $R(R^+)PO_2^-,M^+$ |
| Nitroamide salts | $RN^-NO_2,M^+$ |
| Trisulfonylmethide salts | $RSO_2(CH_3SO_2)_2C^-,M^+$ |
| Xanthate salts | $RSCS_2^-,M^+$ |

TABLE 2

Cationic Hydrophilic Groups

| Functional Group | General Formula |
| --- | --- |
| Quaternary ammonium salts | $RN^+(CH_3)_3,X^-$ |
| Primary, secondary, and tertiary ammonium salts | $RN^+H_n(CH_3)_{3-n}, X^-$ |
| N-alkylpyridinium salts | $RNC_5H_5^+,X^-$ |
| Quaternary phosphonium salts | $RP^+(CH_3)_3,X^-$ |
| Ternary sulfonium salts | $RS^+(CH_3)_2,X^-$ |
| Ternary sulfoxonium salts | $RS^+(\rightarrow O)(CH_3)_2,X^-$ |
| Bis(phosphoranylidyl)ammonium salts | $[R(CH_3)_3P\rightarrow N\leftarrow P(CH_3)_3R]^+,X^-$ |

TABLE 3

Zwitterionic Hydrophilic Groups

| Functional Group | General Formula |
| --- | --- |
| Ammonioacetates | $R(CH_3)_2N^+CH_2CO_2^-$ |
| Ammonio hexanoates | $R(CH_3)_2N^+(CH_2)_5CO_2^-$ |
| Ammonio alkanesulfonates | $R(CH_3)_2N^+(CH_2)_3SO_3^-$ |
| Ammonioalkyl sulfates | $R(CH_3)_2N^+(CH_2)NOSO_3^-$ |
| Trimethylammonioethyl alkylphosphonates | $RPO_2^-OCH_2CH_2N^+(CH_3)_3$ |
| Trimethylammonioethyl-phosphate acylglyceryl esters | $RCO_2CH_2CH(OH)CH_2OPO^-O(CH_2)_2N^+(CH_3)_3$ |

TABLE 4

Dipolar Hydrophilic Groups

| Functional Group | General Formula |
| --- | --- |
| Aliphatic amine oxides | $R(CH_3)_2N\rightarrow O$ |
| Phosphine oxides | $R(CH_3)_2P\rightarrow O$ |
| Phosphonate esters | $R(CH_3O)_2P\rightarrow O$ |
| Phosphate esters | $RO(CH_3O)_2P\rightarrow O$ |
| Amine oxides | $R(CH_3)_2As\rightarrow O$ |
| Sulfoxides | $R(CH_3)S\rightarrow O$ |
| Sulfoximines | $R(CH_3)S(\rightarrow O)\rightarrow NH$ |
| Sulfone diimines | $R(CH_3)S(\rightarrow NH)_2$ |
| Ammonioamidates | $RC(O)N-N+(CH_3)_3$ |
| Amides | $RC(O)N(CH_3)_2$ |

TABLE 5

Single Bond Hydrophilic Groups

| Functional Group | General Formula |
| --- | --- |
| Primary Amines | $RNH_2$ |

In Tables 1–5, R represents a hydrocarbon group, preferably an alkyl group. M represents a metal atom. The subscript n is 1, 2, or 3. X represents a halogen atom. The groups in Tables 1–5 are exemplary and not intended to limit the scope of this invention set forth in the claims. One skilled in the art would be able to select appropriate hydrophilic groups without undue experimentation.

Suitable lipophilic groups include monovalent hydrocarbon groups, substituted monovalent hydrocarbon groups, and siloxanes. Suitable monovalent hydrocarbon groups have 6 to 22 carbon atoms, preferably 8 to 22 carbon atoms, more preferably 10 to 18 carbon atoms. Substituted monovalent hydrocarbon group include halogenated monovalent hydrocarbon groups, typically having 6 to 22 carbon atoms. The monovalent hydrocarbon groups and substituted monovalent hydrocarbon groups can be saturated or unsaturated, branched or unbranched. Preferred branched hydrocarbon groups typically have 8 to 22 carbon atoms. Preferred linear hydrocarbon groups have 8 to 18 carbon atoms.

Suitable lipophilic groups are disclosed in International Patent Publication No. WO 99/12640 at page 12–13. One skilled in the art would be able to select appropriate lipophilic groups without undue experimentation.

Suitable amphiphiles for ingredient (B) also include those disclosed in U.S. Pat. No. 5,756,108. These include 3,7,11, 15-tetramethyl-1,2,3-hexadecanetriol, phytanetriol, N-2-alkoxycarbonyl derivatives of N-methylglucamine, and unsaturated fatty acid monoglycerides.

Suitable amphiphiles for ingredient (B) include surfactants having HLB values of 2.1 to 4.6, see Porter, M. R., *Handbook of Surfactants*, $2^{nd}$ ed., Blackie Academic & Professional, pp. 188–236.

A preferred class of surfactants for use as ingredient (B) comprise monoglycerides having the general formula:

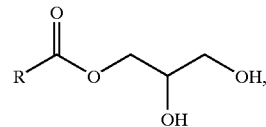

wherein R is selected from the group consisting of monovalent hydrocarbon groups of 6 to 22 carbon atoms, preferably 8 to 22 carbon atoms, more preferably 10 to 18 carbon atoms; and monovalent halogenated hydrocarbon groups of 6 to 22 carbon atoms. The monovalent hydrocarbon groups can be saturated or unsaturated, branched or unbranched. Preferred branched hydrocarbon groups typically have 8 to 22 carbon atoms. Preferred linear hydrocarbon groups have 8 to 18 carbon atoms. Preferred monoglycerides have a melting point $\geq 4020$ C. International Patent Publication No. WO 99/12640 discloses suitable amphiphiles that can form cubic liquid crystalline phase at pages 12–13 and 28–31.

Preferred amphiphiles for ingredient (B) include monoglyceride surfactants such as glycerol monooleate (HLB of 3.8), glycerol monostearate (HLB 3.4), ethoxylated alcohol surfactants such as $C_{12}EO_2$, $C_{12}EO_{23}$, and $C_{16}EO_3$, wherein EO represent an ethylene oxide group, (see Lynch et al., "Aqueous Phase Behavior and Cubic Phase-Containing Emulsions in the C12E2-Water System," *Langmuir*, Vol. 16, No. 7, pp. 3537–3542 (2000)), monolinolein, and combinations thereof.

As long as the monoglyceride has sufficient purity to form cubic liquid crystalline phase in combination with solvent and the hydrotrope, the monoglyceride is suitable for ingredient (B). The monoglyceride is typically greater than about 40% to 100% pure, preferably about 82.5 to 100% pure. However, monoglycerides having purity less than about 40% may also be suitable.

Some diglyceride and triglyceride impurities can prevent the monoglycerides from forming cubic liquid crystalline phases. Therefore, the monoglycerides are preferably free of amounts diglyceride and triglyceride impurities high enough to prevent the monoglycerides from forming cubic liquid crystalline phases.

Suitable monoglycerides are known in the art and are commercially available. Preferred monoglycerides include glycerol monooleate available under the tradename DIMODAN® from Danisco A/S doing business as Grindsted Products A/S of Denmark.

Solvent

Ingredient (C) is a solvent. Ingredient (C) can be polar or nonpolar. Suitable polar solvents include water, glycerol, polyglycols such as polyethylene glycol, formamides such as formamide, n-methyl formamide and dimethylformamide, ethylammonium nitrate, and combinations thereof. Suitable nonpolar solvents include oily solvents such as hydrocarbons and substituted hydrocarbons (e.g., halogenated hydrocarbons). Hydrocarbons are exemplified by alkanes and fatty esters such as lanolin. The solvent must not break down liquid crystals, therefore, some amphiphilic oils and fatty acid diglycerides are unsuitable for use as the solvent.

The amounts of each ingredient in the precursor depend on the phase behavior of the specific ingredients selected. Cubic gel precursor comprises a composition wherein the amounts of ingredients (A), (B), and (C) match any area of the phase diagram not already comprising cubic phase (i.e., containing no cubic phase alone and no cubic phase in equilibrium with another phase). One skilled in the art would be able to select appropriate amounts of each ingredient without undue experimentation by using a phase diagram, as exemplified in FIG. 1.

FIG. 1 represents a ternary phase diagram 100 of a ternary system of (A) ethanol 103, (B) monoolein 106, and (C) water 109. Single phases (other than cubic phases) can be used as a precursor. For example, compositions falling in the single phase regions of the phase diagram, such as the isotropic liquid region 124 and the lamellar region 121, are suitable precursors. Compositions falling in the multiple phase region 112 wherein cubic phase does not form are also suitable as precursors. Compositions that do not fall in the Pn3m cubic phase region 115 and the Ia3d cubic phase region 118 are suitable precursors. (See Luzzati et al., *J. Mol. Biol.*, 229, 540–551 (1993) for a description of the types of cubic phases, including Pn3m and Ia3d cubic phases.)

The precursor can be used in an application where formation of cubic phase is desired under a certain set of conditions (i.e. the presence of sweat, saliva, or other material that will change the system composition such that it is in the area surrounding either of the two cubic phases 115, 118 or within the two cubic phases 115, 118). As a result, the mass fractional composition of the system of components (A), (B), and (C) relative to each other needs to simply obey the following equation:

$$1.0 = a+b+c$$

wherein a is the mass fraction of ingredient (A), b is the mass fraction of ingredient (B), and c is the mass fraction of ingredient (C). and $1.0>a>0$, $1.0>b>0$, $1.0>c \geq 0$. Preferably, a, b, and c are all greater than zero, however when c is 0, the system is a binary system of hydrotrope and amphiphile. In a preferred embodiment of the invention, the precursor is a composition falling within the isotropic liquid region (e.g., region 124 in FIG. 1) on the phase diagram.

The mass fractions of ingredients (A), (B), and (C) in the cubic gel precursor depend on various factors including the specific compounds selected for ingredients (A), (B), and (C). However, typically, $0.5 \geq a \geq 0.05$, $0.8 \geq b \geq 0.1$, and $0.8 \geq c \geq 0$. Preferably, the mass fraction of ingredient (A) is high enough such that a mixture of ingredients (A) and (B) forms an isotropic liquid at 25° C.

Phase diagrams such as that shown in FIG. 1 can be used for any system comprising ingredients (A), (B), and (C) to determine the amounts of each ingredient in the cubic gel precursor, bulk cubic gels, and cubic gel particle dispersions of this invention. Phase diagrams can be obtained by one skilled in the art without undue experimentation using, for example, the methods disclosed by Laughlin, R. G., *The Aqueous Phase Behavior of Surfactants*, Academic Press, Inc., 1994, pp. 521–546.

The cubic gel precursor of this invention may be used to directly form either bulk cubic gel, dispersed cubic gel particles, or a combination of the two, all depending on the desires of the formulator.

Bulk Cubic liquid Crystalline Gel

This invention further relates to a bulk cubic liquid crystalline gel comprising:
 (A) a hydrotrope,
 (B) an amphiphile capable of forming a cubic liquid crystalline phase, and
 (C) a solvent,
 wherein ingredients (A), (B), and (C) are present in mass fractions relative to each other such that $$1.0 = a+b+c$$

wherein a is the mass fraction of ingredient (A), b is the mass fraction of ingredient (B), and c is the mass fraction of ingredient (C), and wherein $1.0>a>0$, $1.0>b>0$, $1.0>c>0$; and with the proviso that a, b, and c fall within a cubic liquid crystalline phase region on a phase diagram representing phase behavior of ingredients (A), (B), and (C).

The mass fractions of ingredients (A), (B), and (C) in the bulk cubic gel depend on various factors including the specific compounds selected for ingredients (A), (B), and (C). However, typically, $0.1 \geq a \geq 0.005$, $0.75 \geq b \geq 0.45$, and $0.6 \geq c \geq 0.1$.

Ingredients (A), (B), and (C) are as described above for the cubic gel precursor. However, the amounts of ingredients (A), (B), and (C) differ, such that the system forms bulk cubic gel. The amount of each ingredient in the bulk cubic gel depends on the phase behavior of the specific ingredients selected. One skilled in the art would be able to select appropriate amounts for each ingredient without undue experimentation by using a phase diagram. The amount of each ingredient must be such that the combined ingredients will form a cubic liquid crystalline phase or a cubic liquid crystalline phase in combination with one or more other phases. Any combination of the amounts of the ingredients that fall within the cubic liquid crystalline region in the phase diagram will be suitable for this invention. For example, referring to FIG. 1 again, the amounts of water 109, ethanol 103, and monoolein 106 must be such that they fall in one of the cubic phase regions 115, 118 in the phase diagram.

Dispersed Cubic Liquid Crystalline Gel Particles

This invention further relates to cubic liquid crystalline gel particles, and dispersions thereof. The cubic liquid crystalline gel particles have the same composition as that described above for the bulk cubic gel, however, the form differs. The particles have a particulate form, rather than a bulk gel. The particles typically range in size from 10 micrometers to 50 nanometers. The dispersion comprises:

(A) a hydrotrope, (B) an amphiphile capable of forming a cubic liquid crystalline phase, and (C) a solvent, wherein ingredients (A), (B), and (C) are present in mass fractions relative to each other such that $$1.0 = a + b + c$$

wherein a is the mass fraction of ingredient (A), b is the mass fraction of ingredient (B), and c is the mass fraction of ingredient (C), and wherein $1.0 > a > 0$, $1.0 > b > 0$, $1.0 > c > 0$; and with the proviso that a, b, and c fall within a region representing cubic liquid crystalline phase in combination with at least one other phase on a phase diagram representing phase behavior of ingredients (A), (B), and (C), with the proviso that the dispersion has the form cubic liquid crystalline gel particles dispersed in the other phase. (Referring again to FIG. 1, dispersions according to this invention fall within the region representing cubic liquid crystalline phase in combination with another phase 127 on the phase diagram 100.)

The mass fractions of ingredients (A), (B), and (C) in the dispersions depend on various factors including the specific compounds selected for ingredients (A), (B), and (C). However, typically, $0.1 \geq a \geq 0.005$, $0.3 \geq b \geq 0.03$, and $0.9 \geq c \geq 0.6$.

The cubic liquid crystalline gel particles, and dispersions thereof, comprise ingredients (A), (B), and (C), described above, and preferably (D) a stabilizer. Suitable stabilizers include water-soluble polymers such as Poloxamer 407 or Carbomer cellulosic polymer, sub-micron or micron-sized solid particles such as clays or crystalline waxes, or coatings of lamellar liquid crystalline phases on the cubic liquid crystalline particle surfaces.

Suitable water-soluble polymers include polyoxyethylene polyoxypropylene copolymers such as Poloxamer 407, which is a polyoxyethylene polyoxypropylene block copolymer of the formula $HO(CH_2CH_2O)_x(CH(CH_3)CH_2))_y(CH_2CH_2O)_zOH$ wherein the average values of x, y, and z are 98, 67, and 98, respectively. Poloxamer 407 is known in the art and commercially available as HODAG® Nonionic 1127-F, from Lambent Technologies Inc., of Norcross, Ga.; PLURACARE® F-127 from BASF Corporation of Parsippany, N.J.; SYNPERONIC® PE/F-127 from Imperial Chemical Industries, PLC., of London, England; MACOL® 27 from Mazer Chemicals, Inc., of Gurnee, Ill.; and PLURONIC® F-127 from Wyandotte Chemicals Corporation of Wyandotte, Mich.

Carbomer cellulosic polymer is a homopolymer of acrylic acid crosslinked with an allyl ether of pentaerythritol or an allyl ether of sucrose. Carbomer cellulosic polymer is available as SYNTHALEN® from 3V Sigma of Milan, Italy and CARBOPOL® from the B.F. Goodrich Company of New York, N.Y.

Suitable (D) stabilizers are disclosed in the *C.T.F.A. International Cosmetic Ingredient Dictionary*, 4th ed., ed. J. M. Nikitakis, et al., The Cosmetic, Toiletry, and Fragrance Association, Washington, D.C.; and in Evans, *The Colloidal Domain*, 2nd ed., Wiley, N.Y., pp. 575–588 (1999).

The amount of ingredient (D) added is typically 1 to 2% based on the weight of ingredient (C).

Methods of the Invention

This invention further relates to methods for preparing the cubic gel precursor, bulk cubic liquid crystalline gel, and dispersed cubic liquid crystalline gel particles described above.

Cubic Gel Precursor

A preferred method for preparing the cubic gel precursor of this invention comprises the steps of:

1) combining ingredients (A) the hydrotrope with (B) the amphiphile, both described above, and 2) optionally adding (C) the solvent described above, wherein the amounts of each ingredient in the composition are as described above.

The precursor does not form cubic gel by itself.

In step 1), the hydrotrope and amphiphile can be combined by any convenient means. When ingredient (B) is a liquid, ingredients (A) and (B) can be combined by simply mixing. When ingredient (B) is a solid such as monoolein, ingredients (A) and (B) are preferably combined by heating ingredient (B) to a temperature greater than its melting point and then combining (e.g., mixing) the melted amphiphile with the hydrotrope. The exact temperature depends on the melting point of the specific amphiphile selected for ingredient (B). Alternatively, ingredient (B) can be fragmented into solid particles and then combined with the hydrotrope; or the hydrotrope may be dissolved in an aqueous hydrotrope solution, and the solution combined with ingredient (B) in step 1).

Step 2) can be carried out during or after step 1). Step 2) can be carried out by, for example, mixing by any convenient means. The product of step 2) contains amounts of ingredients (A), (B), and (C) corresponding to any region on the relevant phase diagram where cubic phase does not form. However, the amounts of ingredients (A), (B), and (C) are preferably such that the product of step 1) is an isotropic liquid at 25° C. Referring to FIG. 1, for example, any combination of (A) ethanol, (B) monoolein, and (C) water that falls in the isotropic region 124 of the phase diagram 100 is suitable to use as the precursor.

Bulk Cubic Liquid Crystalline Gel

Bulk cubic liquid crystalline gel can be prepared by applying a stimulus to the precursor prepared as described above. The stimulus can be selected from the group consisting of: a temperature change; a pressure change; addition of a salt; a pH change; addition of a specified material such as additional hydrotrope, amphiphile, or solvent; removal of a specified material such as a portion of the hydrotrope, amphiphile, or solvent; combinations thereof; and others. When an ingredient is added or removed, the result must be to bring the relative amounts of each ingredient into a cubic phase region on the relevant phase diagram. Referring to FIG. 1, for example, adding a sufficient amount of an ingredient selected from the group consisting of (A) ethanol 103, (B) monoolein 106, and (C) water 109 to bring the relative amounts of (A), (B), and (C) into a cubic phase region 115, 118 of the phase diagram 100 will cause bulk cubic liquid crystalline gel to form.

The precursor can be diluted, for example, by mixing the precursor with additional (A) hydrotrope, (B) amphiphile, or (C) solvent. A material can be removed from the precursor by, for example, evaporation.

In an alternative embodiment of the invention, bulk cubic liquid crystalline gel can be prepared directly by combining amounts of ingredients (A), (B), and (C) corresponding to a cubic phase region on the relevant phase diagram.

After formation of the bulk cubic liquid crystalline gel has been completed, the hydrotrope is not always necessary. The hydrotrope may optionally be removed, e.g., by evaporation. All or a portion of the hydrotrope may be removed.

Dispersed Cubic Liquid Crystalline Gel Particles

Dispersed cubic liquid crystalline gel particles can be prepared from bulk cubic gel or directly from the cubic gel precursor.

Preparing a dispersion of cubic gel particles directly from the precursor can be carried out by a method comprising:
1) a dispersing step selected from the group consisting of
   a) dispersing the precursor described above in a solvent, and b) dispersing solvent in the precursor and thereafter diluting; and preferably
2) stabilizing the product of step 1).

Steps a) and b) may be carried out by several alternate methods. These methods include applying fluid shear such as in a shear mill, applying ultrasonic waves, extruding through a small pore membrane (membrane emulsification), cross membrane emulsification, impinging from opposing jets a stream of the precursor and a stream of solvent, using a static mixer, or combining streams of solvent and the precursor in a micro-mixer that utilizes either laminar or turbulent shear flow conditions to disperse the streams. The precursor may also be contacted with solvent (e.g., water) by spraying a fine mist of the precursor into an environment comprising solvent vapors (e.g., a humid environment). Such a spray allows the formation of droplets with a surface coating of cubic liquid crystalline phase. The droplets can then be collected in bulk in water to disperse the particles and complete their conversion to cubic liquid crystalline gel particles. Alternatively, solvent (e.g. water) can be added to the precursor by bubbling vaporized solvent (e.g., steam) into the precursor. The product of step 1) is an dispersion of cubic liquid crystalline gel particles that is unstable against aggregation.

The product of step 1) is stabilized (i.e., sterically stabilized), for example, by adding (D) a stabilizer described above, or by forming a coating of lamellar liquid crystalline phase on the surfaces of the particles. The product of step 1) may also be stabilized by direct dispersion into a viscous aqueous matrix such as that formed by a water-soluble stabilizer such as Carbomer cellulosic polymer. The product of step 2) is a dispersion of colloidally stable cubic liquid crystalline gel particles.

In an alternative embodiment of the invention, steps 1) and 2) are combined. Steps 1) and 2) are combined by adding (D) the stabilizer to (C) the solvent to form a stabilizing composition and thereafter combining the stabilizing composition with the product of step 1).

Ingredient (A) the hydrotrope may or may not be desirable in the final product, and ingredient (A) is not always necessary once cubic liquid crystalline gel particles form. Therefore, this method may further comprise optional step 3). Step 3) comprises removing ingredient (A) after step 2). Ingredient (A) may be removed by, for example, dialysis and flash evaporation.

In an alternative embodiment of the invention, the precursor may be diluted to form an intermediate such as a dispersion of lamellar liquid crystalline particles, vesicles, or an easily dispersed emulsion. Any of these intermediates can be used to form a colloidally stable dispersion of cubic liquid crystalline gel particles by further dilution in combination with any of the above dispersion and stabilization techniques in steps 1) and 2). This is because the dispersions may be formed and stabilized prior to particle formation. This offers the advantages that intermediates are easier to disperse and stabilize than the potentially more viscous dispersions, and once stabilized, the resulting stabilized intermediates can be diluted to form cubic liquid crystalline gel particles that require no further stabilization.

Alternatively, cubic gel particles can be prepared by fragmenting the bulk cubic gel. Fragmenting the bulk cubic gel can be carried out by, for example, subjecting the bulk cubic gel to shear in a shear mill, ultrasonication, micromixer dispersal, or membrane emulsification. However, if too much energy input is carried out, the cubic liquid crystalline structure of the particles can physically degrade, so care must be exercised when fragmenting the bulk cubic gel. When the structure of the particles degrades, other structures, such as vesicles, can form.

Figure 2:
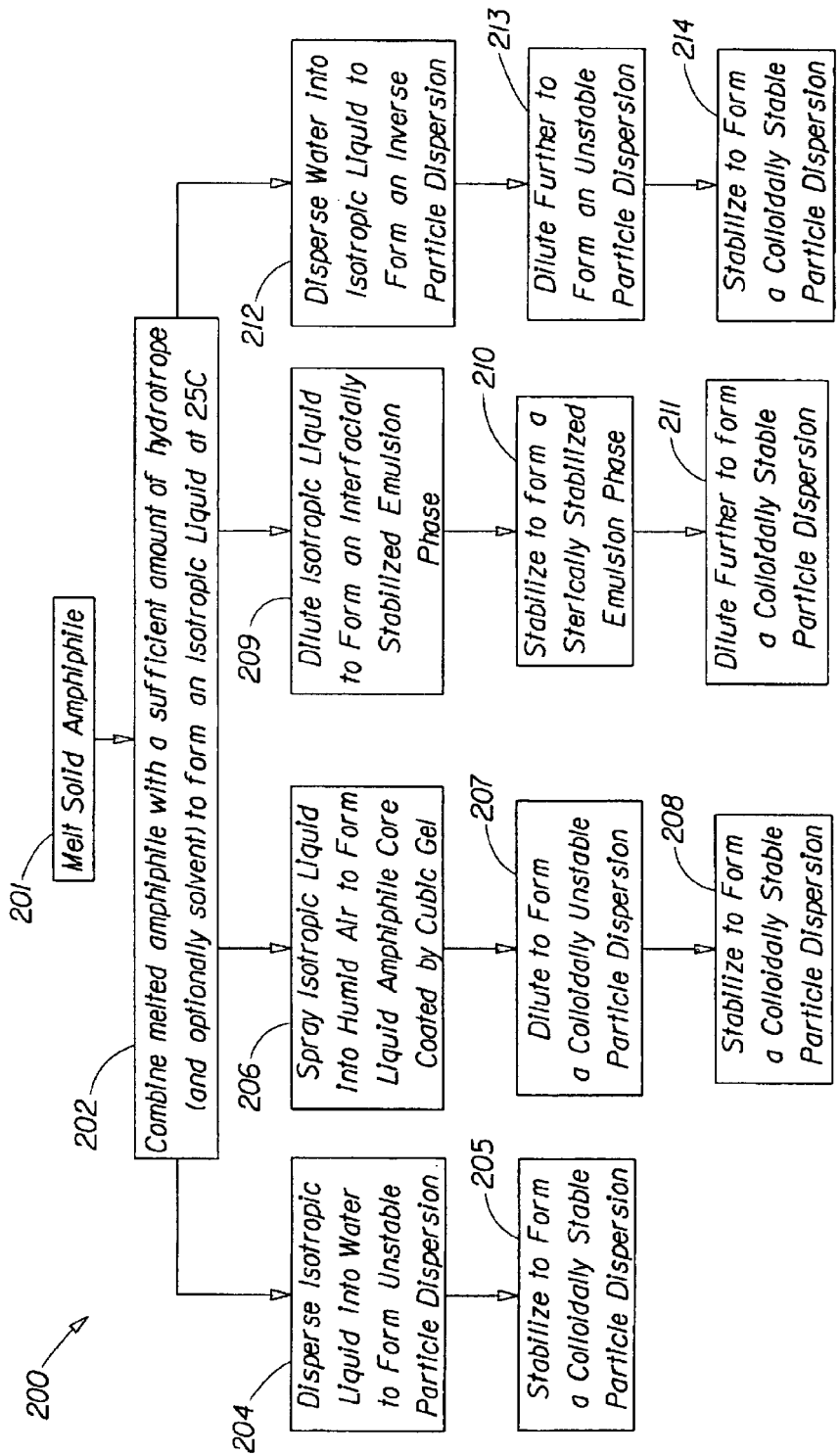
FIG. 2 is a flow diagram of the method steps for the preferred methods for preparing dispersions of cubic gel particles according to this invention.

FIG. 2 is a flow diagram 200 showing methods for preparing dispersions of cubic gel particles according to the preferred embodiments of this invention. In each method, a solid amphiphile is first melted 201 by heating to a temperature greater than or equal to its melting point. Next, the amphiphile is combined with a hydrotrope, and optionally a solvent 202. The combination comprising the amphiphile and hydrotrope, with or without solvent, forms an isotropic liquid at 25° C. After this, there are 4 potential preferred routes for preparing dispersions of cubic gel particles.

In the first route, the isotropic liquid is dispersed into water 204, thereby forming a colloidally unstable dispersion of cubic gel particles. The unstable dispersion is then stabilized 205, by the methods described above.

In the second route, the isotropic liquid is sprayed into humid air 206. This forms droplets comprising a liquid core comprising the amphiphile coated by cubic gel phase material. The droplets are diluted 207 with sufficient water to form a colloidally unstable dispersion of cubic gel particles. Thereafter, the resulting mixture is stabilized 208, by the methods described above.

In the third route, the isotropic liquid is diluted with sufficient water to form an interfacially stabilized emulsion phase 209. The emulsion phase is sterically stabilized by a method described above 210. Thereafter, the stabilized emulsion phase is further diluted with additional water to form a colloidally stable particle dispersion 211.

In the fourth route, water is dispersed into the isotropic liquid to form an inverse particle dispersion 212 (i.e., droplets of water dispersed in the isotropic liquid, rather than cubic phase particles dispersed in water). Thereafter, the inverse dispersion is further diluted with more water to form a colloidally unstable particle dispersion 213. The unstable particle dispersion is stabilized by a method described above 214.

After preparing a dispersion, the particles may optionally be isolated therefrom by any conventional means. For example, the particles can be isolated by removing a sufficient amount of an ingredient selected from the group consisting of (C) the solvent and a combination of (C) the solvent and (A) the hydrotrope. The particles may be dried by evaporation. Alternatively, the particles may be removed from the dispersion by centrifugation or filtration.

Figure 3:
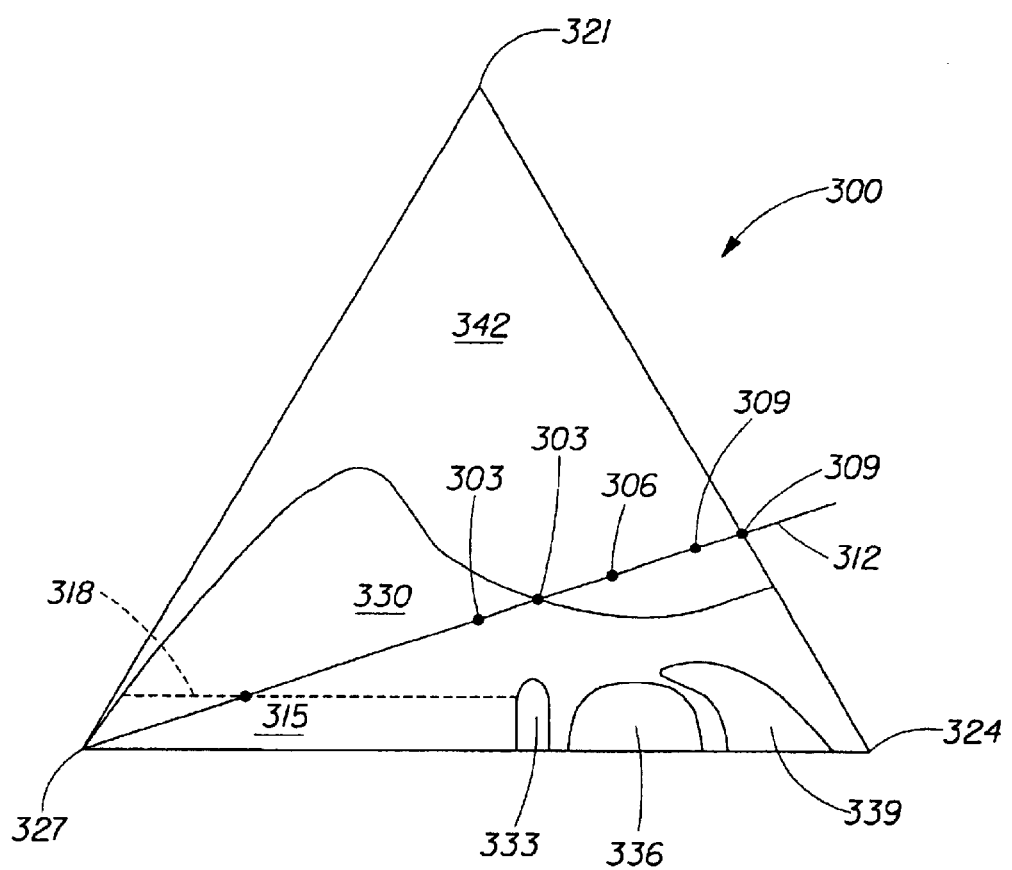
FIG. 3 is a ternary phase diagram showing the phase behavior of ethanol, monoolein, and water.
Figure 4:
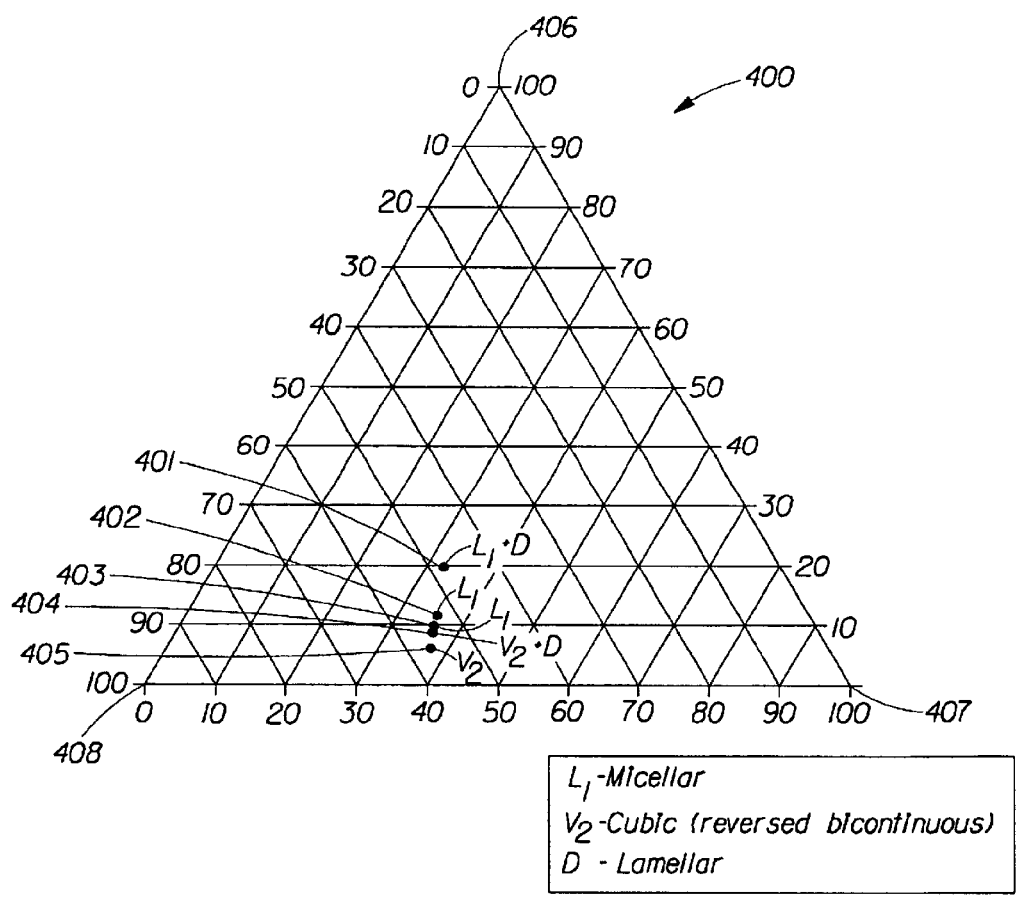
FIG. 4 is a ternary phase diagram showing the phase behavior of ethanol, monoolein, and water.
Figure 5:
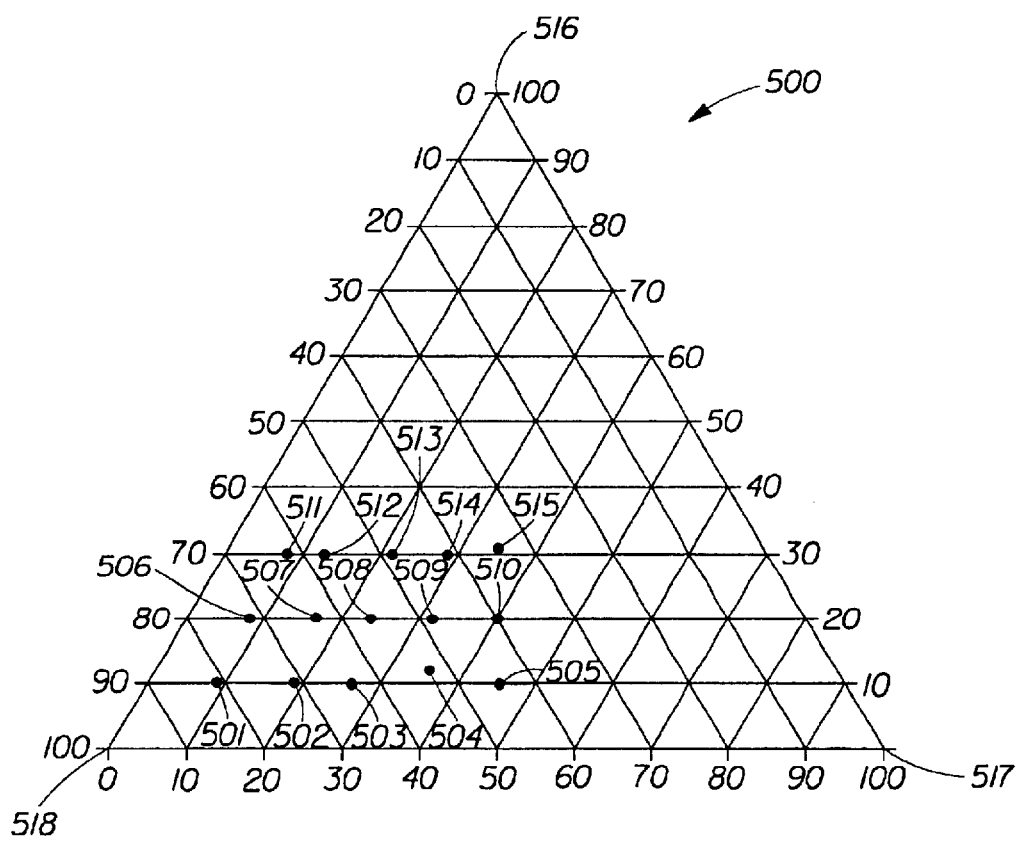
FIG. 5 is a ternary phase diagram showing the phase behavior of 1,2-hexanediol, monoolein, and water.
Figure 6:
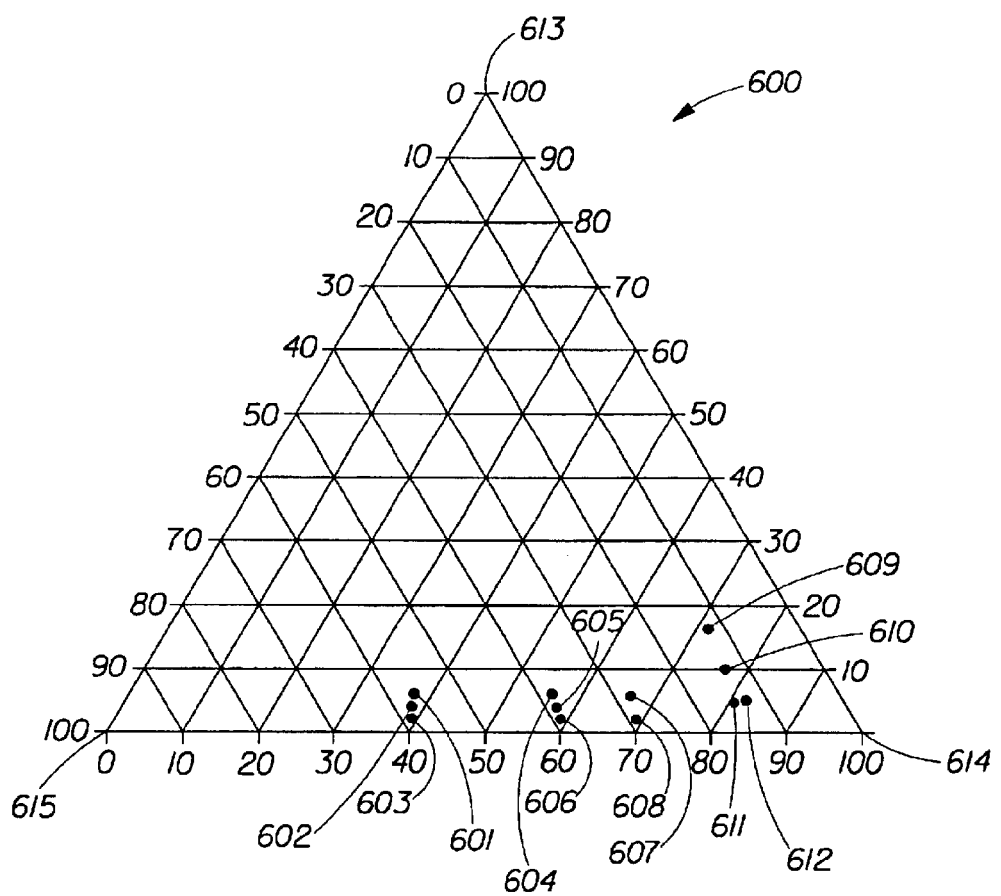
FIG. 6 is a ternary phase diagram showing the phase behavior of 1,2-hexanediol, monoolein, and water.
Figure 7:
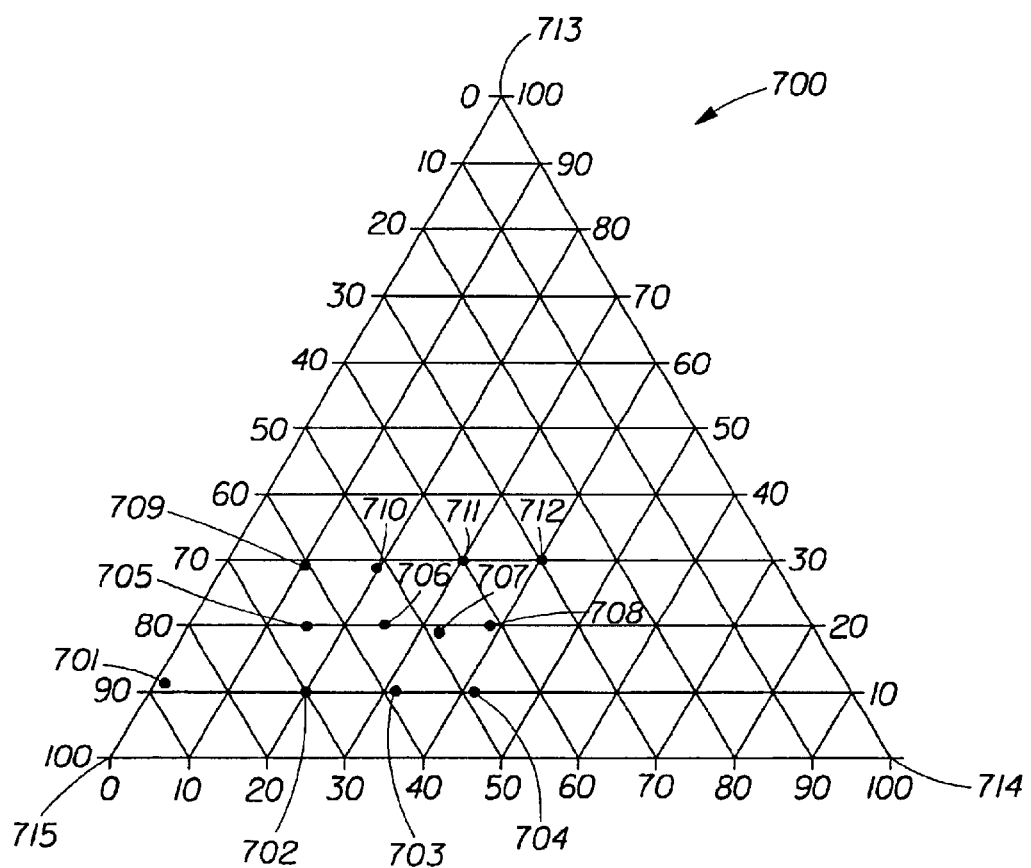
FIG. 7 is a ternary phase diagram showing the phase behavior of ethanol, monoolein, and water.

FIG. 3 is a ternary phase diagram 300 showing the phase behavior of ethanol 321, monoolein 324, and water 327.

Single phases (other than cubic phases) can be used as a precursor. For example, compositions falling in the single phase regions of the phase diagram, such as the isotropic liquid region 342 and the lamellar region 339, are suitable precursors. Precursors can be diluted with one or more ingredients to form bulk cubic gels falling in the Pn3m cubic phase region 333 or the Ia3d cubic phase region 336. Precursors can also be diluted to form cubic gel particle dispersions falling in the multiple phase region 330. The phase diagram 300 can be used to carry out the above methods. For example, a precursor 309 falling in the isotropic liquid region 342 can be prepared as described above. The precursor 303, 306, or 309 can be diluted to form a dispersion of cubic gel particles 315 by adding solvent 327.

Furthermore, the yield of processes producing all forms of cubic phase (bulk cubic gels, dispersions of cubic gel particles) can be predicted using the phase diagram 300. By pre-determining the desired end fraction of cubic phase, the starting and ending points on a phase trajectory 312 can be determined and a process developed from the trajectory 312. If, for example, a suspension of about 60% (w/w) cubic gel particles is desired, the ending point 315 of a phase trajectory 312 must lie on an equilibrium tie line 318 between the isotropic liquid phase region 342 and a cubic phase region 333. Dilution with solvent 327 is represented by a straight line 312 drawn from the starting point to the solvent 327 corner of the phase diagram 300. The starting point of the above dilution process can fall anywhere on a line 312 drawn from the solvent 327 corner through the midpoint of a cubic-liquid tie line 318 and out through the phase diagram 300.

The particles formed in the dispersions typically have particle sizes in the range of about 10 nanometers to about 100 micrometers. However, the exact particle size range depends on the method used to make the particles. For example, particles prepared from precursors that are isotropic liquids typically have sizes in the range of about 10 to about 500 nanometers. Particles prepared from precursors that are emulsions typically have sizes in the range of about 100 nanometers to about 100 micrometers.

Methods of Use

The precursors of this invention can be used as anti-wetting agents. For example, a precursor can be placed between sheets of tissue to provide an absorbent core in, for example, diapers and pads. With the addition of liquid, the precursor forms bulk cubic gel to hold the liquid.

The bulk cubic gels of this invention can be used to generate trans-membrane protein crystal structures.

In a preferred embodiment of the invention, the precursors, bulk cubic gels, and particularly the dispersions and cubic gel particles of this invention are used as delivery vehicles in topical pharmaceutical and cosmetic compositions. The compositions may further comprise one or more pharmaceutically active ingredients, such as non-steroidal anti-inflammatory drugs (e.g., ketoprofen), or cosmetic ingredients, such as perfumes or dyes. In a more preferred embodiment of the invention, the active ingredient also has hydrotropic properties and may be used in addition to the hydrotrope described above as component (A). Alternatively, the active ingredient may be used instead of component (A), or instead of a portion of component (A). Compositions containing an active ingredient can be prepared by the methods described above, wherein the active ingredient is added concurrently with component (A).

In one embodiment of the invention, the precursors, gels, dispersions, and particles described above can be used as delivery vehicles for active ingredients such as pharamceutically active ingredients, agrochemicals, and others. Suitable agrochemicals include pesticides, herbicides, and others. The pesticides and herbicides may be water-soluble or oil-soluble and may be incorporated into the ternary system as an active ingredient with hydrotropic properties or as an active ingredient separate from the hydrotrope.

Examples of suitable pesticides include organophosphates such as diazinon and non-organophosphates such as diclofop-methyl, terrazole, vinclozolin, atrazine, oxamyl propargite, and triallate. Examples of suitable herbicides include atrazine, nicosulfuron, carfentrazone, imazapyr, benefin, and acifluorfen.

In a preferred embodiment of the invention, the controlled release delivery of active ingredients, including agrochemicals such as herbicides and pesticides to a substrate such as a plant or insect surface may be carried out using cubic gel precursors in two main ways: evaporation and dilution. The uniqueness of the evaporation and dilution processes is their ability to produce a "responsive" liquid that provides targeted delivery of an active ingredient in response to some specified stimulus, such as dilution by residual moisture or evaporation as a consequence of spraying. Evaporation and dilution processes may be represented by a line drawn from a starting point to an ending point on the ternary phase diagram.

Dilution

In the dilution process, the starting point is any previously described precursor region on the phase diagram and the ending point is any region of single-phase cubic liquid crystal or multiple-phase (in which at least one phase is cubic liquid crystal). The trajectory of a dilution path will be determined by a straight line drawn between the starting point and the solvent apex of a ternary phase diagram. Once the starting point is chosen, the ending point falls along that straight line.

In one embodiment of the dilution process, a mixture of amphiphile and either an active ingredient with hydrotropic properties or a separate active in combination with a hydrotrope is combined to form an isotropic liquid precursor. The precursor is then sprayed onto a substrate coated with solvent, such as a leaf surface coated with residual moisture (i.e., dew droplets). Spraying disperses the precursor into small droplets that coat the substrate and contact the solvent. Mixing of the solvent on the substrate, e.g., the water on the leaf, with the precursor constitutes dilution and drives the droplet system into the cubic+solvent region of the phase diagram, producing a coating of solvent, active ingredient, and cubic liquid crystalline material which slowly releases the active ingredient into the substrate. Monoglycerides are preferred as the amphiphile in the precursor for plant applications because it is thought that monoglycerides will enhance leaf surface penetration by the active ingredients.

Evaporation

Evaporation is similar to dilution in that the starting point on the ternary phase diagram is also a precursor from which solvent and/or hydrotrope is evaporated to drive the system to an ending point on the phase diagram in a region of single-phase cubic liquid crystal or multiple-phase (in which at least one phase is cubic liquid crystal). In the case of evaporation, choosing a starting point dictates that the process trajectory will progress toward the amphiphile apex of the phase diagram. The exact path taken will be a function of the vapor pressure of the mixture of the solvent and the hydrotrope, and may not be linear as in the case of dilution. Evaporation may occur during spraying and/or after deposition onto the target substrate.

In one embodiment of the evaporation process, a mixture of amphiphile, hydrotrope, solvent, and active ingredient is combined to form an isotropic liquid precursor. The precursor is then sprayed onto a substrate such as a leaf surface. Spraying disperses the precursor into small droplets, increasing their surface area and thus their ability to evaporate solvent and/or hydrotrope. As the solvent and/or hydrotrope evaporate, the droplet system rapidly passes into the cubic liquid crystalline regions of the ternary phase diagram, again producing a coating of solvent, active, and cubic liquid crystalline material which slowly releases the active into the substrate such as the leaf surface. Monoglycerides are preferred as the amphiphile in the precursor for plant applications because it is thought that monoglycerides will enhance leaf surface penetration by the active ingredients.

This invention offers the further advantage that pore size of the cubic liquid crystalline materials (i.e., bulk cubic gels, cubic gel particles, and dispersions of cubic gel particles) can be controlled. Pore size depends on the amount of component (A). In general, pore size increases as the amount of component (A) increases.

EXAMPLES

These examples are intended to illustrate the invention to those skilled in the art and should not be interpreted as limiting the scope of the invention set forth in the claims.

Reference Example 1—Determination of Hydrotrope Utility

A compound for use as a hydrotrope is dissolved in water in amounts to form a hydrotrope solution. The solution is added to monoolein (DIMODAN® MO90K) to yield a composition. The composition is left to equilibrate overnight at a temperature of 25 to 30° C.

Polarized light microscopy (PLM) is used to determine whether the composition exhibits birefringence or distinct textures. PLM can be carried out on a polarized light microscope or constructed light box, as described by Laughlin, R. G., *J. Colloid Interface Sci.*, 55, 239–242 (1976). Rheological properties of the composition are also observed. Compositions containing a viscous phase that exhibits no birefringence and no distinct textures by PLM form cubic phase. Formation of cubic phase means that the compound is suitable to use as a hydrotrope in this invention at the amount of the compound specified.

Examples 1 to 4 and Comparative Examples 1 to 5

Various compounds are evaluated according to Reference Example 1. The compounds, the compositions prepared, and the results are in Table E1, below. FIG. 4 is a ternary diagram 400 showing the data points in Example 3. FIG. 5 is a ternary diagram 500 for 1,2-hexanediol 516, monoolein 517, and water 518. FIG. 5 shows the data points 501–515 and phases formed at each point in Comparative Example 2. FIG. 6 is a ternary diagram 600 for 1,2-hexanediol 613, monoolein 614, and water 615. FIG. 6 shows the data points 601–612 and phases formed at each point in Comparative Example 3. FIG. 7 is a ternary diagram 700 for ethanol 713, monoolein 714, and water 715. FIG. 7 shows the data points 701–712 and phases formed at each point in Example 4 and Comparative Example 4.

TABLE E1

Hydrotrope Test Results

| Example | Compound | FIG. NO. | Point No. | Amount of Compound (κ) | Amount of Water (κ) | Amount of Amphiphile (κ) | Phase(s) Formed |
|---|---|---|---|---|---|---|---|
| Ex. 1 | ethanol | 4 | 404 | 9 | 55 | 36 | cubic and lamellar |
| | | | 405 | 6 | 56 | 38 | cubic and lamellar |
| Comp. Ex. 1 | ethanol | 4 | 401 | 20 | 48 | 32 | L1 and lamellar |
| | | | 402 | 12 | 53 | 35 | L1 |
| | | | 403 | 10 | 54 | 36 | L1 |
| Ex. 2 | 1,4-butanediol | | | 10 | 80 | 10 | cubic and L1 |
| | procaine hydrogen chloride | | | 10 | 80 | 10 | cubic and L1 |
| Comp. Ex. 2 | 1,2-hexanediol | 5 | 501 | 10 | 81 | 9 | liquid water and L1 |
| | | | 502 | 10 | 71 | 19 | L1 and lamellar |
| | | | 503 | 10 | 64 | 26 | L1 and lamellar |
| | | | 504 | 12 | 53 | 35 | L1 and lamellar |
| | | | 505 | 10 | 45 | 45 | L1 and lamellar |
| | | | 506 | 20 | 72 | 8 | L1 |
| | | | 507 | 20 | 64 | 16 | L1 |
| | | | 508 | 20 | 56 | 24 | L1 |
| | | | 509 | 20 | 49 | 31 | L1 |
| | | | 510 | 20 | 40 | 40 | L1 and lamellar |
| | | | 511 | 30 | 63 | 7 | L1 |
| | | | 512 | 30 | 56 | 14 | L1 |
| | | | 513 | 30 | 49 | 21 | L1 |
| | | | 514 | 30 | 42 | 28 | L1 |
| | | | 515 | 30 | 34 | 36 | L1 |
| Ex. 3 | 1,2-hexanediol | 6 | 601 | 6 | 56 | 38 | cubic and lamellar |
| | | | 602 | 4 | 58 | 38 | cubic and lamellar |
| | | | 603 | 2 | 59 | 39 | cubic and lamellar |

TABLE E1-continued

Hydrotrope Test Results

| Example | Compound | FIG. NO. | Point No. | Amount of Compound (κ) | Amount of Water (κ) | Amount of Amphiphile (κ) | Phase(s) Formed |
|---|---|---|---|---|---|---|---|
| | | | 604 | 6 | 38 | 56 | cubic and lamellar |
| | | | 605 | 4 | 39 | 57 | cubic and lamellar |
| | | | 606 | 2 | 39 | 59 | cubic and lamellar |
| | | | 607 | 6 | 28 | 66 | cubic and lamellar |
| | | | 608 | 2 | 29 | 69 | cubic and lamellar |
| Comp. Ex. 3 | 1,2-hexanediol | 6 | 609 | 16 | 13 | 71 | lamellar |
| | | | 610 | 10 | 14 | 76 | lamellar |
| | | | 611 | 5 | 14 | 81 | lamellar |
| | | | 612 | 5 | 12 | 83 | lamellar |
| Ex. 4 | ethanol | 7 | 701 | 11 | 88 | 1 | cubic & isotropic liquid |
| | | | 702 | 10 | 70 | 20 | cubic & isotropic liquid |
| | | | 703 | 10 | 59 | 31 | cubic & isotropic liquid |
| | | | 704 | 10 | 48 | 42 | cubic & isotropic liquid |
| Comp. Ex. 4 | ethanol | 7 | 705 | 20 | 65 | 14 | L1 |
| | | | 706 | 20 | 55 | 25 | L1 and lamellar |
| | | | 707 | 19 | 49 | 32 | L1 and lamellar |
| | | | 708 | 20 | 42 | 39 | lamellar |
| | | | 709 | 29 | 60 | 11 | L1 and lamellar |
| | | | 710 | 28 | 52 | 20 | L1 and lamellar |
| | | | 711 | 30 | 40 | 30 | lamellar |
| | | | 712 | 30 | 29 | 41 | lamellar |
| Comp. Ex. 5 | 2-propanol | | | 10 | 80 | 10 | Turbid solution and L1 phase |

Example 1 and Comparative Example 1, and Example 4 and Comparative Example 4, show that ethanol can be used as a hydrotrope in a system with monoolein and water according to this invention, when the ethanol is present at relatively low levels (i.e., less than or equal to 10% of the system). Comparative Example 1 and Comparative Example 4 show that when the amount of ethanol is too high, (above about 10 or 11%), the system does not form cubic phase. Example 4 shows that ethanol is a preferred hydrotrope for use in this invention because in a system of ethanol, monoolein, and water, cubic phase in equilibrium with liquid water can be formed.

Example 2 shows that 1,4-butanediol and procaine hydrogen chloride are effective as hydrotropes in a system with monoolein and water according to this invention.

Example 3 shows that 1,2-hexanediol is suitable to use as a hydrotrope in a system with monoolein and water according to this invention. However, Example 3, and Comparative Examples 2 and 3 show that 1,2-hexanediol does not form cubic phase in equilibrium with liquid water at the practical amounts of 1,2-hexanediol used in this invention.

Comparative Example 5 shows that 2-propanol is not preferred to use as a hydrotrope in a system of monoolein and water according to this invention because the system does not form cubic phase when 10% 2-propanol is present.

Reference Example 2—Cryo-Transmission Electron Microscopy

Samples were evaluated to determine whether cubic phase had formed by cryo-TEM. For cryo-TEM, the samples were prepared in a controlled environment vitrification system (CEVS) which is described in detail by Bellare, J. R.; Davis, H. T.; Scriven, L. E.; Talmon, Y., Controlled environment vitrification technique, *J. Electron Microsc. Tech.*, 1988, 10, 87–111. A 3 μl drop of the sample solution was placed on a carbon-coated holey polymer support film mounted on a standard 300-mesh TEM grid (Ted Pella, Inc.). The drop was blotted with filter paper until it was reduced to a thin film (10–200 nm) spanning the holes (2–8 μm) of the support film. The sample was then vitrified by rapidly plunging it through a synchronous shutter at the bottom of the CEVS into liquid ethane at its freezing point. The vitreous specimen was transferred under liquid nitrogen into a Philips CM120 transmission electron microscope for imaging. The temperature of the sample was kept under −170° C. throughout the examination.

Reference Example 3—Small Angle X-ray Scattering (SAXS)

SAXS is a technique that measures the fluctuations in electron density in a material over the size range of about 1000–5 nm, which makes it suitable to characterize structures in a sample over this spatial range. SAXS consists of illuminating a sample with a collimated beam of x-rays of the appropriate wavelength and measuring the distribution of intensity scattered. If the structures are periodic, SAXS is particularly well suited to assess the type of periodicity and its dimensions. Periodic distributions in matter in a material will cause periodic distribution of scattered intensity over the appropriate angular range.

SAXS was performed on samples with CuKα radiation ($\lambda$=0.154 nm) generated with a Rigaku RU-300 rotating anode. The generator was operated at 40 kV and 40 mA with a 0.2×0.2 mm focal size (a 0.2×2 mm filament run in point mode). The patterns were collected with the Siemens 2-dimensional small angle scattering system which consists of the HI-STAR wire detector and Anton Parr HR-PHK collimation system. Collimation is achieved with a single 100 mm diameter pinhole 490 mm from the focal spot. The size of the focal spot restricts bean divergence. A 300 mm guard pinhole is placed 650 mm from the focal spot, just in front of the sample. The detector is placed a distance of 650 mm from the sample. Ni filters were used to eliminate the Kβ radiation. Because of the small beam size and large sample-to-detector distance, two dimensional profiles (qx, qy) can be obtained with a minimum of instrumental smearing, so no smearing corrections were employed.

Example 5

A bulk cubic gel according to this invention is prepared by melting 50% monoolein, adding 2% ethanol, and then adding 48% water. The sample is analyzed according to the method in Reference Example 3. The results are in Table E2.

Comparative Example 6

A dispersion of cubic gel particles is prepared as in Example 5, except that ethanol was omitted. The sample is analyzed according to the method in Reference Example 3. The results are in Table E2.

Comparative Example 7

Predicted values for Pn3m cubic phase of a system of monoolein and water were obtained. See Funari, S. S. and Gert, R., "X-ray Studies on the C12EO2/Water System", *J. Phys. Chem. B* 1997, 101, 732 and Winey, Thomas and Fetters, "Morphologies in Binary Blends", *J. Chem. Phys.* 1991, Vol. 95, No. 12, Pg. 9368. The results are in Table E2.

TABLE E2

Comparison of peak spacing form SAXS data for monoolein/water systems with that predicted froin Pn3m cubic phase.

| Miller Index of Reflection | Example 5 $d_{hkl}/d_{110}$ | Comparative Example 6 $d_{hkl}/d_{110}$ | Comparative Example 7 $d_{hkl}/d_{110}$ |
| --- | --- | --- | --- |
| 110 | 1.00 | 1.00 | 1.00 |
| 111 | 0.819 | 0.816 | 0.816 |
| 200 | 0.707 | 0.704 | 0.707 |
| 211 | 0.574 | 0.573 | 0.577 |
| 220 | 0.495 | 0.496 | 0.500 |

The Miller Index describes the symmetry of the liquid crystalline structures. The ratio $d_{hkl}/d_{110}$ represents the angular position of one peak relative to the primary peak (110). Peaks spaced at about the same intervals as those shown in Comparative Example 7 have the same structure as Comparative Example 7. Example 5 and Comparative Examples 6 and 7 show that the periodic structure and type of structure of the bulk cubic gel according to this invention correspond well to the periodic structure and type of structure of known cubic phase materials consisting of monoolein and water. Therefore, the compositions of this invention form cubic phase.

Example 6

A precursor is formed by melting 0.5 g monoolein and mixing in 0.5 g ethanol to form a clear, low viscosity (isotropic) liquid. 9.0 g of water are added. A colloidally unstable dispersion of 9% cubic phase particles in 91% water forms. This is illustrated in FIG. 9.

Figure 9:
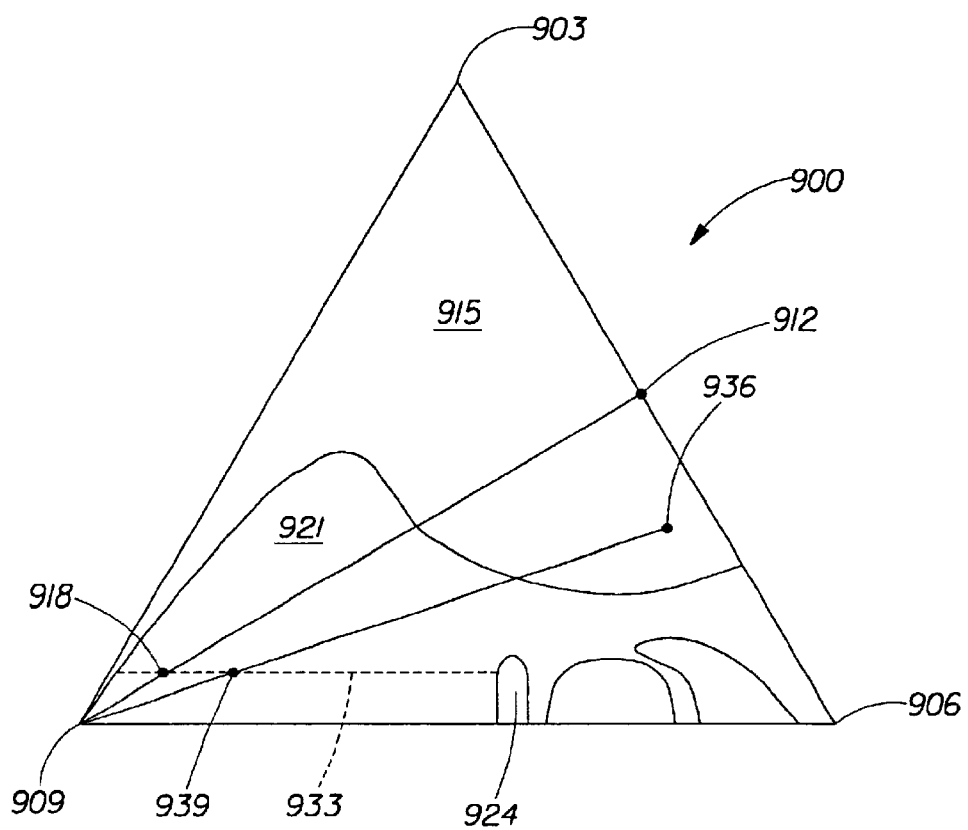
FIG. 9 is a phase diagram showing the phase behavior of ethanol, monoolein, and water in Example 6.

FIG. 9 is a phase diagram 900 showing the phase behavior of ethanol 903, monoolein 906, and water 909. The precursor 912 falls within the isotropic liquid region 915 of the phase diagram 900. The dispersion 939 falls within a multiple phase region 921 wherein cubic phase is present with liquid water. The dispersion 918 falls on an equilibrium tie line 933 between the isotropic liquid phase region 915 and the Pn3m cubic phase region 924.

Example 7

1.0 g monoolein is melted and mixed with 0.5 g ethanol and 0.18 g water to form a clear, low viscosity (isotropic) liquid 936. 8.4 g of water are added. A colloidally unstable dispersion of 22% cubic phase particles and 78% water forms. This is also illustrated in FIG. 9. FIG. 9 is a phase diagram 900 showing the phase behavior of ethanol 903, monoolein 906, and water 909. The precursor 936 falls within the isotropic liquid region 915 of the phase diagram 900. The dispersion 918 falls within a multiple phase region 921 wherein cubic phase is present with liquid water. The dispersion 939 falls on an equilibrium tie line 933 between the isotropic liquid phase region 915 and the Pn3m cubic phase region 924.

Example 8

Figure 8A:
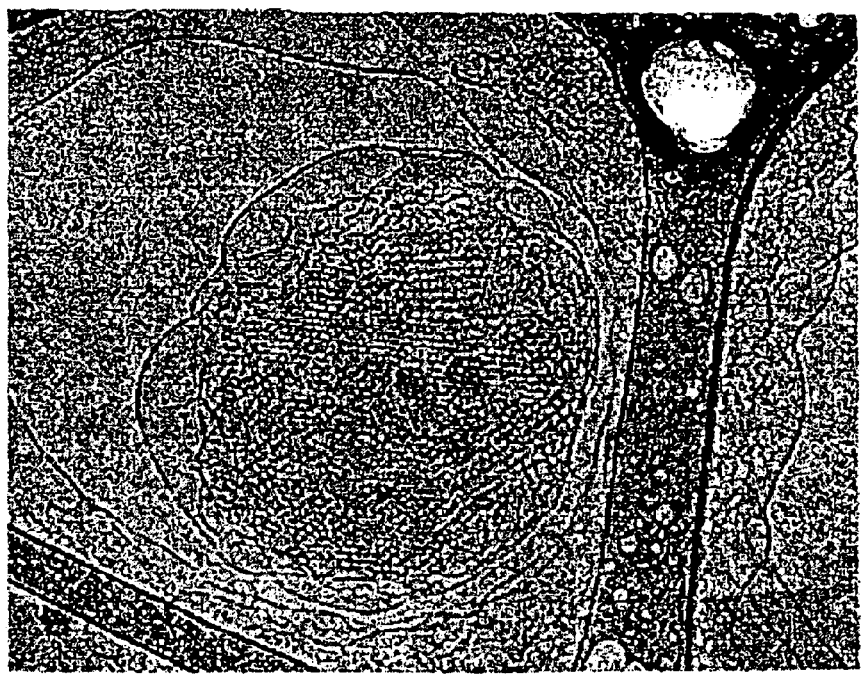
FIG. 8a is a cryo-TEM image of a cubic gel particle prepared according to Example 8 of this invention.

0.5g ethanol is mixed with 0.5 g melted monoolein to form a clear, low viscosity (isotropic) liquid. 9.0 g of a 1.2% polymer (Poloxamer 407) solution is added. A colloidally stable dispersion of 9% cubic phase particles and 91% water and polymer forms. A cryo-TEM image was obtained by the method of Reference Example 2. The image is in FIG. 8a.

Example 9

1.0 g monoolein is melted and mixed with 0.5 g ethanol and 0.18 g water to form a clear, low viscosity (isotropic) liquid. 8.4 g of a 1.2% polymer (Poloxamer 407) solution are added. A colloidally stable dispersion of 22% cubic phase particles and 78% water and polymer forms.

Examples 7–10 show that dispersions of cubic gel particles can be successfully prepared according to the methods of this invention.

Example 10

A precursor 1012 is prepared by mixing 0.20 g melted monoolein and 0.40 g ethanol to form a clear liquid. An intermediate in the form of a macroemulsion having both large (i.e., 5–10 μm diameter) particles as well as small (i.e. 100–150 nm in diameter) particles is formed by adding 1.40 g water. Particle diameter is measured by optical microscopy. The particles under a microscope are photgraphed and compared to photographs of calipers with 1 micrometer divisions. The emulsion is diluted by adding 4.24 g water. A colloidally unstable dispersion of cubic liquid crystalline particles 1036 forms. This is illustrated in FIG. 10.

Figure 10:
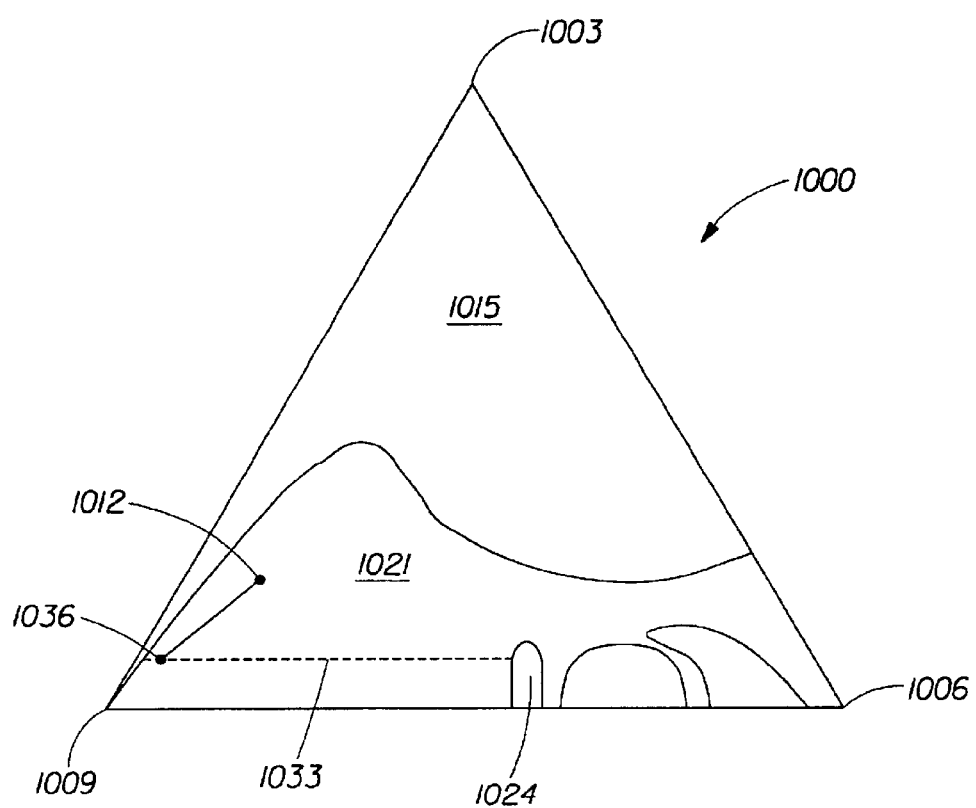
FIG. 10 is a phase diagram showing the phase behavior of ethanol, monoolein, and water in Example 10.

FIG. 10 is a phase diagram 1000 showing the phase behavior of ethanol 1003, monoolein 1006, and water 1009. The precursor 1012 falls within the multiple phase region 1021 of the phase diagram 1000. The dispersion 1036 falls within a multiple phase region 1021 wherein cubic phase is present with liquid water. The dispersion 1036 falls on an equilibrium tie line 1033 between the isotropic liquid phase region 1036 and the Pn3m cubic phase region 1024.

Example 11

A precursor is prepared by mixing 0.20 g melted monoolein and 0.40 g ethanol to form a clear liquid. An intermediate in the form of an emulsion having a narrower particle size distribution than that of Example 10 is prepared by adding 1.40 g water to form an emulsion. The emulsion is sheared for five minutes in a high shear mill at 15,000 RPM to reduce the particle size. The emulsion is diluted by adding 4.24 g water. A colloidally unstable dispersion of cubic liquid crystalline particles forms.

Example 12

Figure 8B:
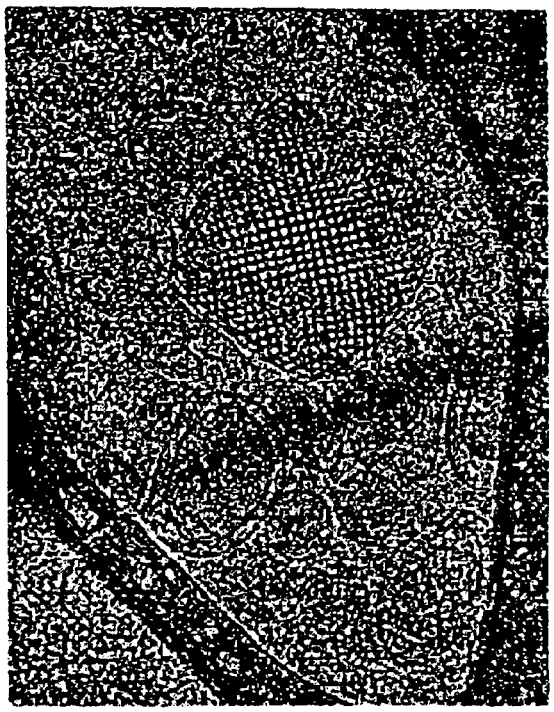
FIG. 8b is a cryo-TEM image of a cubic gel particle prepared according to Example 12 of this invention.

Example 10 is repeated, except that rather than adding 4.24 g water to dilute the emulsion, 4.24 g of an aqueous polymer (Poloxamer 407) solution is used instead. This substitution causes a colloidally stable dispersion to form, and the presence of the polymer does not affect the phase behavior of the system in that cubic phase still forms. A cryo-TEM image was obtained by the method of Reference Example 2. The image of a cubic gel particle formed in the dispersion is in FIG. 8b. Example 12 shows that the dispersions prepared according to the methods of this invention (with the hydrotrope present) form cubic liquid crystalline gel phase particles.

Example 13

Example 11 is repeated except that rather than adding 4.24 g water to dilute the emulsion, 4.24 g of an aqueous polymer (Poloxamer 407) solution is used instead. This substitution causes a colloidally stable dispersion to form, and the presence of the polymer does not affect the phase behavior of the system.

Example 14

5.0 g ethanol, 25.0 g melted monoolein, and 70.0 g water are mixed directly. A colloidally unstable dispersion of cubic liquid crystalline particles forms.

Example 15

5.0 g ethanol, 25.0 g melted monoolein, and 70.0 g of a 1.5% polymer (Poloxamer 407) solution are combined directly. A colloidally stable dispersion of cubic liquid crystalline particles forms.

Examples 11–15 show that dispersions of cubic gel particles can be successfully prepared according to the methods of this invention.

Example 16

A cubic gel precursor is prepared by mixing 40.0 g ethanol with 30.0 g melted monoolein. An isotropic liquid precursor forms. Example 16 shows that cubic gel precursors can be prepared according to the methods of this invention.

Example 17

5.0 g ethanol and 68.0 g melted monoolein are mixed and form an isotropic liquid. 27.0 g water is added. A viscous, isotropic bulk cubic liquid crystalline gel forms. Example 17 shows that bulk cubic liquid crystalline gels can be prepared according to the methods of this invention.

Example 18

Figure 8C:
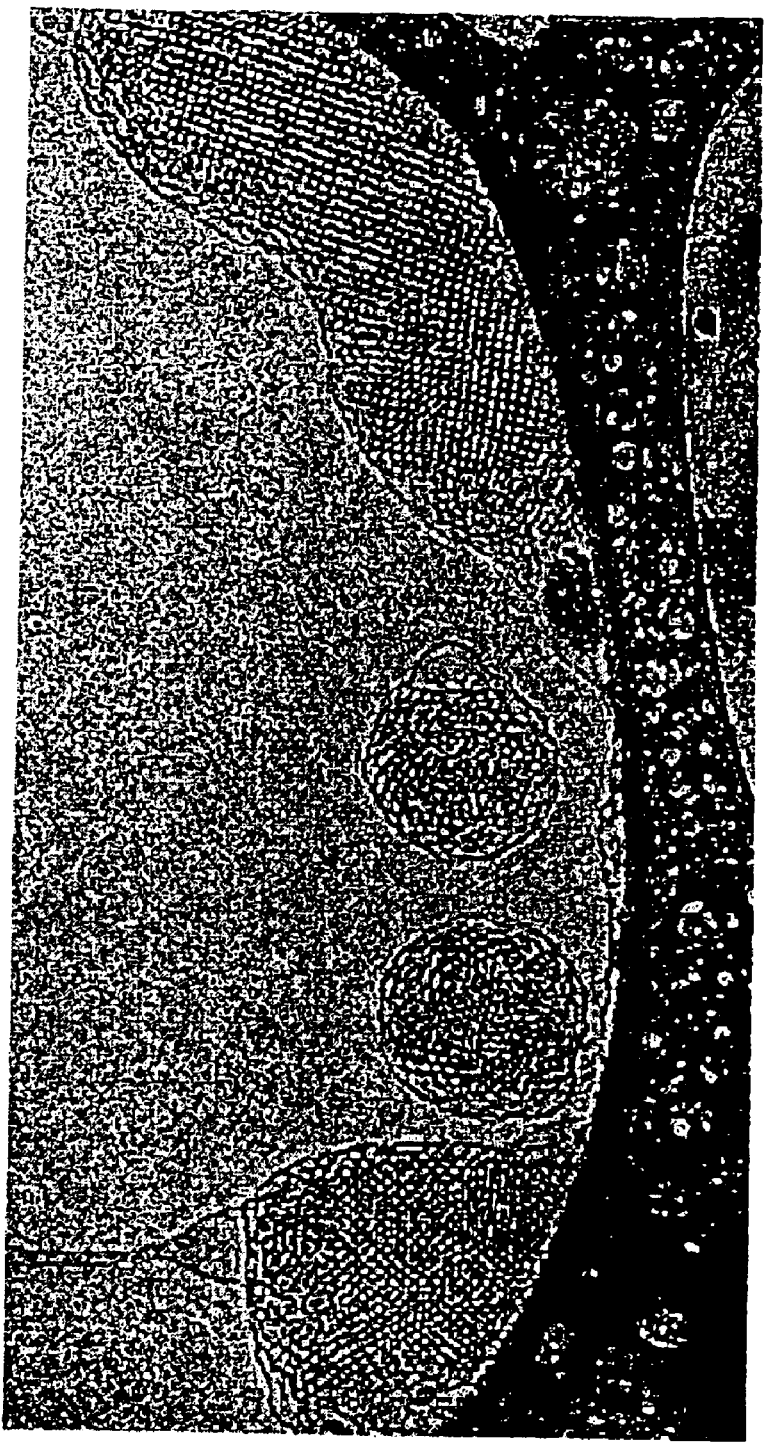
FIG. 8c is a cryo-TEM image of cubic gel particles prepared according to Example 18 of this invention.

Cubic gel particles are prepared from the bulk cubic gel prepared in Example 17 by applying ultrasonic energy for 5 minutes. Images of the particles were obtained by the method of Reference Example 2. The images are in FIG. 8c.

Example 19

A precursor is prepared by mixing 10.465 g monoolein with 4.45831 g water until cubic phase formed. The cubic phase is diluted to L1 phase with 17.2242 g ethanol, and 0.0042 Sudan II red dye is added to form a solution. The solution is put into a spray bottle and sprayed on the leaves of a mono- and poly-saccharides; copolymers of ethylene oxide and propylene oxide; fatty acid ethoxylates; sorbitan derivatives; sodium butyrate; nicotinamide; procaine hydrogen chloride; and ethylene glycol, propylene glycol, glycerol, and polyglyceryl esters, and the ethoxylated derivatives thereof; and combinations thereof.

9. The gel of claim 6, wherein ingredient (B) is a monoglyceride having the formula:

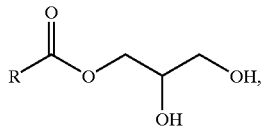

wherein R is selected from the group consisting of monovalent hydrocarbon groups of 6 to 22 carbon atoms, and monovalent halogenated hydrocarbon groups of 6 to 22 carbon atoms.

10. The gel of claim 6, wherein ingredient (C) is a polar solvent selected from the group consisting of water, glycerol, glycols, formamides, ethylammonium nitrate, and combinations thereof.

11. A dispersion comprising:
   (A) a hydrotrope,
   (B) an amphiphile capable of forming a cubic liquid crystalline phase, and
   (C) a solvent,
   wherein ingredients (A), (B), and (C) are present in mass fractions relative to each other such that $$1.0 = a+b+c$$

wherein a is the mass fraction of ingredient (A), b is the mass fraction of ingredient (B), and c is the mass fraction of ingredient (C), and wherein $1.0>a>0$, $1.0>b>0$, $1.0>c>0$; and with the proviso that a, b, and c fall within a region representing cubic liquid crystalline phase in combination with at least one other phase on a phase diagram representing phase behavior of ingredients (A), (B), and (C), with the proviso that the dispersion is formed as cubic liquid crystalline gel particulates dispersed in the other phase.

12. The dispersion of claim 11, wherein $0.1 \geq a \geq 0.005$, $0.3 \geq b \geq 0.03$, and $0.9 \geq c \geq 0.6$.

13. The dispersion of claim 11, wherein ingredient (A) is selected from the group consisting of: low molecular weight alcohols; polyols; alcohol ethoxylates; surfactants derived from mono- and poly-saccharides; copolymers of ethylene oxide and propylene oxide; fatty acid ethoxylates; sorbitan derivatives; sodium butyrate; nicotinamide; procaine hydrogen chloride; and ethylene glycol, propylene glycol, glycerol, and polyglyceryl esters, and the ethoxylated derivatives thereof; and combinations thereof.

14. The dispersion of claim 11, wherein ingredient (B) is a monoglyceride having the formula:

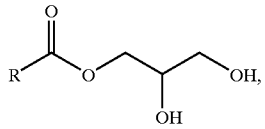

wherein R is selected from the group consisting of monovalent hydrocarbon groups of 6 to 22 carbon atoms, and monovalent halogenated hydrocarbon groups of 6 to 22 carbon atoms.

15. The dispersion of claim 11, wherein ingredient (C) is a polar solvent selected from the group consisting of water, glycerol, glycols, formamides, ethylammonium nitrate, and combinations thereof.

16. The dispersion of claim 11, further comprising (D) a stabilizer.

17. Cubic liquid crystalline gel particles comprising:
   (A) a hydrotrope,
   (B) an amphiphile capable of forming a cubic liquid crystalline phase,
   (C) a solvent, and
   (D) a stabilizer,
   wherein ingredients (A), (B), and (C) are present in relative mass fractions relative to each other such that $$1.0 = a+b+c$$

wherein a is the mass fraction of ingredient (A), b is the mass fraction of ingredient (B), and c is the mass fraction of ingredient (C), and wherein $1.0>a>0$, $1.0>b>0$, $1.0>c>0$; and with the provisos that a, b, and c fall within a cubic liquid crystalline phase region on a phase diagram representing phase behavior of ingredients (A), (B), and (C), and that ingredients (A), (B), and (C) have a particulate form.

18. The particles of claim 17, wherein ingredient (A) is selected from the group consisting of low molecular weight alcohols; polyols; alcohol ethoxylates; surfactants derived from mono- and poly-saccharides; copolymers of ethylene oxide and propylene oxide; fatty acid ethoxylates; sorbitan derivatives; sodium butyrate; nicotinamide; procaine hydrogen chloride; and ethylene glycol, propylene glycol, glycerol, and polyglyceryl esters, and the ethoxylated derivatives thereof; and combinations thereof.

19. The particles of claim 17, wherein ingredient (B) is a monoglyceride having the formula:

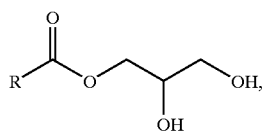

wherein R is selected from the group consisting of monovalent hydrocarbon groups of 6 to 22 carbon atoms, and monovalent halogenated hydrocarbon groups of 6 to 22 carbon atoms.

20. The particles of claim 17, wherein ingredient (C) is a polar solvent selected from the group consisting of water, glycerol, glycols, formamides, ethylammonium nitrate, and combinations thereof.

21. A method for preparing a cubic gel precursor comprising the steps of:
   1) combining (A) a hydrotrope with (B) an amphiphile capable of forming a cubic liquid crystalline phase, and
   2) optionally adding (C) a solvent,
      wherein ingredients (A), (B), and (C) are combined in mass fractions relative to each other such that $$1.0 = a+b+c$$

wherein a is the mass fraction of ingredient (A), b is the mass fraction of ingredient (B), and c is the mass fraction of ingredient (C), and wherein $1.0>a>0$, $1.0>b>0$, $1.0>c\geq 0$; and with the proviso that a, b, and c do not fall within a cubic liquid crystalline phase region on a phase diagram representing phase behavior of ingredients (A), (B), and (C), and with the proviso that amounts of each ingredient in the composition are such that cubic phase gel forms upon occurrence of a stimulus.

22. The method of claim 21, wherein ingredient (B) is a liquid, and ingredients (A) and (B) are combined by mixing.

23. The method of claim 21, wherein ingredient (B) is a solid, and ingredients (A) and (B) are combined by a method selected from the group consisting of:
(a) heating ingredient (B) to a temperature greater than its melting point and then mixing ingredient (B) with ingredient (A),
(b) fragmenting ingredient (B) into solid particles and thereafter combining ingredient (B) with ingredient (A),
(c) dissolving ingredient (A) in an aqueous hydrotrope solution, and combining the solution with ingredient (B).

24. The method of claim 21, wherein step 2) is carried out at a time selected from the group consisting of during and after step 1).

25. The method of claim 21, further comprising:
3) applying the stimulus.

26. The method of claim 25, wherein the stimulus is selected from the group consisting of:
(a) addition of a specified material selected from the group consisting of additional hydrotrope, amphiphile, and solvent,
(b) removal of a material selected from the group consisting of a portion of the hydrotrope, amphiphile, and solvent,
(c) a temperature change,
(d) a pH change,
(e) addition of a salt,
(f) a pressure change, and
(g) combinations thereof.

27. The method of claim 25, further comprising:
4) removing the hydrotrope after step 3).

28. A method for preparing a cubic liquid crystalline gel composition comprising the steps of:
1) combining in a composition, ingredients comprising (A) a hydrotrope and (B) an amphiphile capable of forming a cubic liquid crystalline phase, and
2) mixing the product of step 1) with (C) a solvent,
wherein ingredients (A), (B), and (C) are combined in mass fractions relative to each other such that $$1.0 = a+b+c$$

wherein a is the mass fraction of ingredient (A), b is the mass fraction of ingredient (B), and c is the mass fraction of ingredient (C), and wherein $1.0>a>0$, $1.0>b>0$, $1.0>c>0$; and with the proviso that a, b, and c fall within a cubic liquid crystalline phase region on a phase diagram representing phase behavior of ingredients (A), (B), and (C).

29. The method of claim 28, wherein step 1) is carried out by a method selected from the group consisting of:
a) heating ingredient (B) to a temperature greater than its melting point and then mixing with the hydrotrope,
b) fragmenting ingredient (B) into solid particles and combining the solid particles with the hydrotrope, and
c) dissolving ingredient (A) in an aqueous hydrotrope solution, and combining the solution with ingredient (B).

30. The method of claim 28, wherein step 2) is carried out at a time selected from the group consisting of during and after step 1).

31. The method of claim 28, further comprising:
3) removing the hydrotrope after step 2).

32. A method for preparing a dispersion of cubic gel particles directly from a precursor comprising the steps of:
1) dispersing a cubic gel precursor comprising:
(A) a hydrotrope,
(B) an amphiphile capable of forming a cubic liquid crystalline phase, and optionally
(C) a solvent,
wherein ingredients (A), (B), and (C) are present in mass fractions relative to each other such that $$1.0 = a+b+c$$

wherein a is the mass fraction of ingredient (A), b is the mass fraction of ingredient (B), and c is the mass fraction of ingredient (C), and wherein $1.0>a>0$, $1.0>b>0$, $1.0>c\geq 0$; and with the proviso that a, b, and c do not fall within a cubic liquid crystalline phase region on a phase diagram representing phase behavior of ingredients (A), (B), and (C)
wherein dispersing is carried out by a method selected from the group consisting of
a) dispersing the precursor in additional (C) solvent, and
b) dispersing additional (C) solvent in the precursor, and thereafter diluting.

33. The method of claim 32, wherein step 1a) is carried out by a method selected from the group consisting of:
i) applying fluid shear,
ii) applying ultrasonic waves,
iii) extruding through a small pore membrane,
iv) cross membrane emulsifying,
v) impinging from opposing jets of a stream of the precursor and a stream of solvent, and
vi) combining streams of solvent and the precursor in a micro-mixer.

34. The method of claim 32, wherein step 1b) is carried out by a method selected from the group consisting of:
i) spraying a fine mist of the precursor into an environment comprising solvent vapors, and thereafter diluting;
ii) bubbling vaporized solvent into the precursor, and thereafter diluting.

35. The method of claim 32, further comprising:
2) stabilizing the product of step 1).

36. The method of claim 35, wherein step 2) is carried out by a method selected from the group consisting of:
a) adding (D) a stabilizer,
b) forming a coating of lamellar liquid crystalline phase on surfaces of particles formed in step 1)
c) directly dispersing the product of step 1) into a viscous matrix comprising the stabilizer and solvent.

37. The method of claim 35, wherein steps 1) and 2) are combined by adding (D) the stabilizer to (C) the solvent to form a stabilizing composition and thereafter combining the stabilizing composition with the product of step 1).

38. The method of claim 35, further comprising the step of:
3) removing ingredient (A) after step 2).

39. The method of claim 32, wherein the precursor is diluted prior to step 1).

40. The method of claim 38, further comprising the step of:
4) isolating the particles during or after step 3).

41. A method for preparing a dispersion of cubic liquid crystalline gel particles comprising fragmenting a bulk cubic liquid crystalline gel comprising:
- (A) a hydrotrope,
- (B) an amphiphile capable of forming a cubic liquid crystalline phase, and
- (C) a solvent,
- wherein ingredients (A), (B), and (C) are present in mass fractions relative to each other such that $$1.0 = a+b+c$$

wherein a is the mass fraction of ingredient (A), b is the mass fraction of ingredient (B), and c is the mass fraction of ingredient (C), and wherein 1.0>a>0, 1.0>b>0, 1.0>c>0; and with the proviso that a, b, and c fall within a cubic liquid crystalline phase region on a phase diagram representing phase behavior of ingredients (A), (B), and (C).

42. The method of claim 41, wherein fragmenting can be carried out by a method selected from the group consisting of:
- a) subjecting the bulk cubic liquid crystalline gel to fluid shear,
- b) ultrasonication,
- c) dispersal in a micromixer, and
- d) membrane emulsification.

43. The method of claim 41, further comprising the step of: isolating the particles after fragmentation.

44. A method for preparing dispersions of cubic liquid crystalline gel particles comprising the steps of:
1) heating (B) a solid amphiphile capable of forming a cubic liquid crystalline phase to a temperature greater than or equal to its melting point,
2) combining the product of step 1) with (A) a hydrotrope,
3) adding (C) water,
    wherein ingredients (A), (B), and (C) are present in mass fractions relative to each other such that $$1.0 = a+b+c$$

wherein a is the mass fraction of ingredient (A), b is the mass fraction of ingredient (B), and c is the mass fraction of ingredient (C), and wherein 1.0>a>0, 1.0>b>0, 1.0>c≧0; and with the proviso that a, b, and c fall within an isotropic liquid phase region on a phase diagram representing phase behavior of ingredients (A), (B), and (C)
4) forming a dispersion by a route selected from the group consisting of
   i) dispersing the product of step 3) into (C) the water, and thereafter stabilizing;
   ii) spraying the isotropic liquid into a humid environment, diluting with sufficient water to form a colloidally unstable dispersion of cubic gel particles, and thereafter stabilizing;
   iii) diluting the isotropic liquid with sufficient water to form an interfacially stabilized emulsion phase, sterically stabilizing said emulsion phase, and thereafter, further diluting with additional water; and
   iv) dispersing water into the isotropic liquid, further diluting with sufficient water to form an unstable particle dispersion, and thereafter stabilizing.

45. The method of claim 44, further comprising the step of: 4) removing ingredient (A) after step 3).

46. The method of claim 45, further comprising the step of: 5) isolating the particles.

47. A method for manufacturing a cubic liquid crystalline phase material comprising the steps of:
1) preparing a precursor comprising
   (A) a hydrotrope,
   (B) an amphiphile capable of forming a cubic liquid crystalline phase, and optionally
   (C) a solvent,
   wherein ingredients (A), (B), and (C) are present in mass fractions relative to each other such that $$1.0 = a+b+c$$

wherein a is the mass fraction of ingredient (A), b is the mass fraction of ingredient (B), and c is the mass fraction of ingredient (C), and wherein 1.0>a>0, 1.0>b>0, 1.0>c≧0; and with the proviso that a, b, and c fall at a starting point on a phase trajectory within an isotropic liquid region on a phase diagram representing phase behavior of ingredients (A), (B), and (C);
2) diluting the product of step 1) with ingredient (C) until an end point is reached on the phase trajectory, wherein the end point lies on a tie line between the isotropic liquid region and a cubic phase containing region on the phase diagram.

48. A method for delivering an active ingredient to a substrate comprising:
1) preparing a cubic gel precursor comprising:
   (A) a hydrotrope,
   (B) an amphiphile capable of forming a cubic liquid crystalline phase,
   (C) a solvent, and
   (D) an active ingredient,
   wherein ingredients (A), (B), and (C) are combined in mass fractions relative to each other such that $$1.0 = a+b+c$$

wherein a is the mass fraction of ingredient (A), b is the mass fraction of ingredient (B), and c is the mass fraction of ingredient (C), and wherein 1.0>a>0, 1.0>b>0, 1.0>c≧0; and with the proviso that a, b, and c fall within an isotropic liquid region on a phase diagram representing phase behavior of ingredients (A), (B), and (C), and with the proviso that amounts of each ingredient in the composition are such that cubic phase gel forms upon occurrence of a stimulus; and
2) spraying the precursor onto a substrate.

49. The method of claim 48, wherein the active ingredient is an agrochemical and the substrate is a plant surface.

* * * * *